(12) United States Patent
McDonald et al.

(10) Patent No.: US 8,042,540 B2
(45) Date of Patent: Oct. 25, 2011

(54) PATIENT OXYGEN DELIVERY MASK

(75) Inventors: Lee McDonald, Barrie (CA); Julius Hajgato, Shantybay (CA)

(73) Assignee: Southmedic Incorporated, Barrie (CA)

( * ) Notice: Subject to any disclaimer, the term of this patent is extended or adjusted under 35 U.S.C. 154(b) by 930 days.

(21) Appl. No.: 11/417,988

(22) Filed: May 4, 2006

(65) Prior Publication Data
US 2006/0196510 A1 Sep. 7, 2006

Related U.S. Application Data

(63) Continuation-in-part of application No. 11/038,816, filed on Jan. 20, 2005, now abandoned, which is a continuation-in-part of application No. 10/966,920, filed on Oct. 15, 2004, now abandoned.

(51) Int. Cl.
*A62B 18/02* (2006.01)
*A62B 18/08* (2006.01)

(52) U.S. Cl. ......... 128/206.28; 128/206.27; 128/206.21; 128/205.25; 128/207.11

(58) Field of Classification Search ............. 128/204.18, 128/204.25, 205.25, 206.12, 206.14, 206.21, 128/206.28, 207.18, 200.24, 200.27, 200.28, 128/201.22–201.29, 202.28, 203.29, 204.11, 128/204.21, 204.26, 204.29, 205.11, 206.23–206.25, 128/206.27, 207.11–207.12
See application file for complete search history.

(56) References Cited

U.S. PATENT DOCUMENTS

| | | | |
|---|---|---|---|
| 2,313,999 A | | 3/1943 | Kreiselman |
| 3,566,866 A | * | 3/1971 | Adams ..................... 128/200.13 |
| 3,683,907 A | | 8/1972 | Cotabish |
| 3,848,617 A | * | 11/1974 | Dray ............................. 137/88 |
| 4,018,221 A | | 4/1977 | Rennie |
| 4,071,025 A | * | 1/1978 | Kohnke ..................... 128/205.13 |
| 4,207,888 A | * | 6/1980 | Ghormley ................ 128/203.29 |
| 4,282,869 A | | 8/1981 | Zidulka |
| 4,465,067 A | | 8/1984 | Koch et al. |
| 4,641,645 A | * | 2/1987 | Tayebi ..................... 128/206.19 |
| 4,961,420 A | * | 10/1990 | Cappa et al. ............. 128/207.12 |

(Continued)

FOREIGN PATENT DOCUMENTS

DE 4307754 A1 4/1994

(Continued)

OTHER PUBLICATIONS

Supplementary European Search Report; Jun. 18, 2010; Munich, Germany; 4 pp.

*Primary Examiner* — Justine Yu
*Assistant Examiner* — Annette Dixon
(74) *Attorney, Agent, or Firm* — C. G. Mersereau; Nikolai & Mersereau, P.A.

(57) ABSTRACT

A mask for delivery of oxygen to a patient is disclosed, including a body having a peripheral portion, a central portion, and bridge portions extending between the central portion and the peripheral portion. The central portion has an inner surface and an outer surface, the inner surface to be oriented towards the patient's face when the mask is in position, the inner surface of the central portion being provided with a wall circumscribing a base. The wall and base circumscribe a centrally positioned oxygen delivery aperture or oxygen diffuser to direct the flow of oxygen generally towards the patient's nose and mouth when the mask is in use. An element associated with the aperture and the central portion releasably receives and secures in position an oxygen delivery tube.

17 Claims, 27 Drawing Sheets

U.S. PATENT DOCUMENTS

| | | | |
|---|---|---|---|
| 5,400,781 A * | 3/1995 | Davenport | 128/206.28 |
| 5,687,715 A | 11/1997 | Landis et al. | |
| 5,697,363 A | 12/1997 | Hart | |
| 5,709,204 A * | 1/1998 | Lester | 128/205.25 |
| 6,065,473 A | 5/2000 | McCombs et al. | |
| 6,247,470 B1 | 6/2001 | Ketchedjian | |
| D449,376 S | 10/2001 | McDonald et al. | |
| D449,883 S | 10/2001 | McDonald et al. | |
| 6,450,166 B1 * | 9/2002 | McDonald et al. | 128/206.27 |
| 6,595,207 B1 * | 7/2003 | McDonald et al. | 128/200.28 |
| 6,629,531 B2 * | 10/2003 | Gleason et al. | 128/205.25 |
| 6,675,796 B2 | 1/2004 | McDonald | |
| 6,968,844 B2 * | 11/2005 | Liland et al. | 128/206.16 |
| 2003/0127101 A1 * | 7/2003 | Dennis | 128/206.21 |

FOREIGN PATENT DOCUMENTS

| | | |
|---|---|---|
| EP | 0053449 A1 | 6/1982 |
| WO | 9829153 A1 | 7/1998 |

* cited by examiner

PATIENT OXYGEN DELIVERY MASK

RELATED APPLICATIONS

The present application is a continuation-in-part of application Ser. No. 11/038,816 filed on Jan. 20, 2005, now abandoned, which is a continuation-in-part of application Ser. No. 10/966,920 filed on Oct. 15, 2004, now abandoned.

Claims 1-6 of this application have subject matter disclosed in Ser. No. 10/966,920 filed on Oct. 15, 2004.

Claims 7-15 of this application have subject matter disclosed in Ser. No. 11/038,816 filed on Jan. 20, 2005.

FIELD OF THE INVENTION

The present invention relates to medical equipment, namely a novel mask for delivery of oxygen to a patient, and more particularly to a mask which can be used to replace conventional oxygen masks and nasal cannulae oxygen delivery systems.

BACKGROUND OF THE INVENTION

Conventional oxygen masks comprise tent like structures which are strapped over the nose and mouth of the patient, often using an elastic band or bands behind the patient's ears or head. Oxygen is fed from a supply through a tube into the bottom portion of the mask at the front of the patient. Many problems exist with such masks, including the fact that many patients find them claustrophobic, the mask must be removed for the patient to speak or eat, thereby discontinuing therapy, and the face mask creates irregular and inefficient infusion of oxygen by the patient since exhaled air from the patient is mixed with oxygen in the mask. Oxygen masks can only be used for oxygen flows greater than 4 liters/minute because exhaled gas accumulates in the mask, and, at lower flow rates interferes with delivery of oxygen-enriched air to the patient.

Conventional nasal cannulae oxygen delivery systems employ an oxygen delivery tube with tubular, open ended nasal prongs at the delivery end of the tube for insertion into a patient's nasal passages. The oxygen delivery tube and nasal cannulae are supported in position by a tube wrapped about the patient's ears or head, making the system both difficult to handle and uncomfortable since it applies downward pressure on the patient's ears when the patient is in a seated position. As well, patients often get nose bleeds from the dryness of the oxygen supplied through the nasal cannulae. Patients also get sores on the ears, face and nose due to the direct contact of the oxygen tubing with the skin. Nasal cannulae can only deliver flows of 0.5 to 4 liters/minute.

Of background interest is Ketchedjian, U.S. Pat. No. 6,247,470 issued Jun. 19, 2001 which describes and illustrates an oxygen delivery apparatus comprising a headset to which is pivotally attached, for rotation in one plane, a flexible arm carrying tubular members for passing oxygen to a patient's mouth. The apparatus is also provided with a carbon dioxide monitoring system.

McCombs et al., U.S. Pat. No. 6,065,473 issued May 23, 2000 describes a somewhat similar apparatus, for non-medical purposes, intended to dispense concentrated oxygen to users, the apparatus comprising an oxygen delivery nozzle attached by an arm extending from a flexible head band, to bathe the user's nose and mouth with oxygen, when in use. Laid-open German Application DE 43 07 754 A1, published Apr. 7, 1994, teaches a system for controlled supply or removal of respiratory air from a user, which system incorporates a mask body held by a rigid air tube over the mouth and/or nose of the user, the air tube being pivotally adjustable in one plane, to enable proper positioning of the mask.

U.S. Pat. No. 3,683,907 of Cotabish issued Aug. 15, 1972 describes and illustrates a fresh air respirator, for use for example by miners, which comprises a cup, supported by pivotable arms in front of the face of the user, a stream of air being conducted to the cup to provide fresh air around the user's nose and mouth.

The applicant has developed a number of lightweight oxygen delivery systems for patients, as described for example in U.S. Pat. No. 6,675,796 issued Jan. 13, 2004, U.S. Pat. No. 6,595,207 issued Jul. 22, 2003 and U.S. Pat. No. 6,450,166 issued Sep. 17, 2002. Also, applicant's U.S. Design Patent Nos. D449,376 issued Aug. 16, 2003 and D449,883 issued Oct. 30, 2001 illustrate designs for such devices. All of these references feature oxygen diffuser devices, designed to create a turbulent oxygen flow, to be situated during use in front of the nose and mouth of a patient, and being held in that area by means of a mount such as a head band, to which is secured a rigid, but bendable oxygen delivery tube. The subject matter of each of these references is incorporated herein by reference.

Other references of general background interest include U.S. Pat. No. 4,282,869 of Zidulka issued Aug. 11, 1981, U.S. Pat. No. 4,018,221 of Rennie issued Apr. 19, 1977, U.S. Pat. No. 5,687,715 of Landis et al. issued Nov. 18, 1997, U.S. Pat. No. 4,465,067 of Koch et al. issued Aug. 4, 1984 and U.S. Pat. No. 5,697,363 of Hart issued Dec. 16, 1977, all of which describe and illustrate different types of head mounted apparatus for delivering oxygen or other gases to a patient.

Most of these prior art devices intended for delivery of oxygen to a patient do not provide the ease of usage, both by health care workers and the patient, and reliability against unintended removal or dislodgement from position, as is required to permit widespread use by the health care profession.

It is desirable to provide an oxygen delivery mask system that provides a suitably high oxygen concentration over a wide range of $O_2$ flow rates. This would permit the use of a single mask for a variety of applications, wherein different flow rates are desirable. It is particularly desirable to provide a mask capable of application as a high flow mask, for use with highly compromised patients. It is desirable to provide a range of flow rates in an open mask that does not trap the exhaled air. It is further desirable to provide a mask that may be readily collapsed into a more compact structure for storage and transport, but which easily snaps back into its use position.

It is an object of the present invention to provide a more versatile, reliable and practical system for delivery of oxygen to patients.

SUMMARY OF INVENTION

In accordance with the present invention there is provided an improved mask for delivery of oxygen to a patient. The mask comprises a body having a peripheral portion that forms the mask rim, which when in use sits comfortably on a patient's face. The mask body is generally concave, opening towards the patient's face. The mask body is open in configuration and is further defined by a central portion, and bridge portions extending between the central portion and the peripheral portion and integral therewith. The central portion has an inner surface and an outer surface. The inner surface is oriented towards the patient's face, when the mask is in position, and is contoured so as to sit at a location spaced over the patient's nose and mouth.

An oxygen diffuser extends from the inner surface of the central portion towards the patient's face. The diffuser includes an outer tubular structure formed from a wall circumscribing a base. The term "wall" is used herein for convenience of description and refers to a structure that extends upwardly when the mask is face down. Obviously, when the mask is upright, this component will extend in a generally horizontal orientation. The diffuser wall has a generally concave configuration and circumscribes a centrally positioned oxygen delivery aperture which extends through the central portion between the inner surface and the outer surface. A baffle positioned within the oxygen flow path within the interior of the tubular diffuser wall disrupts the inflowing gas stream to generate turbulence. The diffuser structure directs the flow of oxygen generally towards the patient's nose and mouth when the mask is in use. Acting together, the diffuser wall and baffle generate an oxygen plume which surrounds the patient's nose and mouth. Attachments are provided on opposite sides of the peripheral portion, for securing a flexible strap means to extend behind the patient's head or ears to hold the mask in position when in use. Also, means are associated with the aperture and of the central portion releasably to secure in position an oxygen delivery tube. The bridge portion consists of an array of webs that are arranged to maintain the convex shape of the mask while permitting a substantial open structure, with preferably about half or more of the mask body being open. As will be seen, the open structure has several benefits. For patient comfort, it is less restrictive and permits the patient to eat, talk, etc. As well, the open structure permits exhaled air to readily dissipate.

In a further embodiment of the present invention, the mask additionally includes the oxygen delivery tube. This delivery tube is attached to an elbow, so designed as to swivel in at the attachment point, so that the oxygen supply tube can easily be directed to either side of the patient. It is releasably securable to the outer surface of the central portion of the mask so as to communicate with the oxygen delivery aperture. As well, a baffle is provided, the baffle being constructed so as to be releasably seated over the oxygen delivery aperture on the inner surface of the central portion of the mask. The inner surface of the baffle is configured so as to assist, during use of the mask, in creating turbulence in an oxygen flow leaving the oxygen delivery aperture and assist in mixing oxygen with ambient air and thereby avoid a direct flow of oxygen towards the patient's face.

In yet a further embodiment of the present invention, the mask is further provided with an oxygen/carbon dioxide monitor tube releasably securable to the outer surface of the central portion of the mask, so as to communicate through the oxygen delivery aperture with an area above the inner surface of the central portion during use of the mask for passage of air within the mask to an oxygen/carbon dioxide monitor. The baffle is constructed so as to be releasably seated over the oxygen delivery aperture on the inner surface of the central portion of the mask. The baffle has a concave shaped wall and is configured and positioned so as to assist during use of the mask in creating turbulence in an oxygen flow leaving the oxygen delivery aperture and assist in mixing oxygen with ambient air and thereby avoid a direct flow of oxygen toward a patient's face. A carbon dioxide intake is positioned within the concave shaped wall of the baffle, the carbon dioxide intake communicating with the carbon dioxide monitor tube.

The bridge portions of the mask, from a top of the mask to a bottom of the mask, may be configured in an inverted "Y" shape so that openings are provided towards the bottom and on both sides of the mask for unobstructed access to, and viewing of a patient's mouth and others parts of the patient's face. The bridge portions comprise a web which is spaced apart from the patient's face so as to maintain a sense of openness and lack of confinement for the patient. A suitable spacing is between 12 and 40 mm from the patient's face, for example when measured from the region between the patient's nose and upper lip.

According to another aspect, the bridge portions include a pair of opposing transverse webs, radiating horizontally outwardly from the central portion, when the mask is held in a vertical position, defining openings both above and below each of the transverse webs. It is believed that the use of transverse webs provide improved oxygen concentrations within the mask, across a range of oxygen flow rates being introduced into the mask. Without wishing to be tied to any theory, it is believed that this is accomplished by partially blocking the inflow of entrained ambient air, as oxygen enters the mask, and is particularly effective at relatively high $O_2$ flow rates. The structure still permits the use of substantial openings within the mask body, so as to easily permit exhaled air to be discharged.

According to another aspect, the diffuser wall structure extending from the central portion of the mask extends outwardly by a specified amount so as to generate a plume of oxygen-enriched air surrounding the user's face and nose, across a wide range of flow rates. The diffuser wall has a generally triangular shape when viewed in plan, from the perspective of the user. Preferably, in this version the diffuser wall ranges in height between about 3 and 25 mm, with the wall increasing in height from bottom to top. More particularly, the wall may range in height between 8 and 16 mm. The exposed rim of the wall is generally vertical when the mask is upright, and since the mask body itself angles upwardly and inwardly towards the user, the wall is tapered to accommodate this angle and thus increases in height towards the top of the mask. The diffuser wall structure has a maximum width (left to right when the mask is upright) of about 40 mm at its widest point and maximum height (top to bottom when the mask is upright) of about 80 mm. More preferably, the width is 20-30 mm and height is 17-27 mm. As well, the exposed rim of the wall is curvilinear so as to protrude somewhat towards the user towards the top of the mask.

According to another aspect, at least some and preferably all of the bridge portions include a rib that extends inwardly towards the user's face. The rib joins with the wall portion of the central portion, and extends generally parallel to the orientation of the corresponding bridge. The rib is at its thickest when it joins with the wall, and tapers as it extends towards the rim. The ribs serve a stiffening function to help maintain the shape of the mask while permitting relatively thinner materials for the webs. Further, if the mask body, including the ribs, is fabricated from a suitable resilient material, the ribs permit the mask to be compressed into a relatively flat structure for transport and storage, and to snap back into a suitable concave "use" position. For this purpose, the mask may be stored in a suitable container, such as a bag or ridged or semi-ridged container, such that when opened and the mask removed therefrom, it will snap resiliently into its suitable concave position for use by a patient.

In a further aspect, the oxygen delivery system comprises in general terms a mask for covering a portion of the user's face, having a peripheral rim for contacting the user's face to substantially surround only his mouth and nose region, a web-like mask body and an oxygen diffuser. A fastener such as an elastic strap holds the mask firmly against the user's face so as to cover the nose and mouth region. The body is semi-rigid or more preferably rigid and shaped so as to protrude outwardly away from the user's face to be spaced apart from the user's face. The body supports a gas diffuser and a baffle or other gas obstructing member positioned in the path of the discharged gas so as to direct a turbulent stream of gas towards the user, such as oxygen or an oxygen-rich gas. The diffuser is positioned so as to direct the gas flow towards the user's mouth and nose region at a non-oblique angle so as to generate a plume covering or substantially covering this portion of the user's face. Thus, if the user is upright the gas flow is substantially horizontal. The mask body consists of a web having at least one and preferably a plurality of openings to permit access to the user's face, for example an opening directly opposed to the user's mouth to permit the user to eat, drink and converse normally while wearing the mask, while also permitting medical personnel to easily administer medicines or a thermometer or the like to the patient's mouth.

According to this aspect, a plurality of relatively large openings (together comprising at least about 30% of the surface area of the mask body and preferably at least 50%) also permits rapid discharge and dispersal of exhaled gases to the exterior of the mask. The location, size, number and shape of the openings is dictated at least in part by the desired use of the mask, keeping in mind the comfort and convenience of the user and the needs of medical staff for potential access to the user's mouth or nose. For example, a mask for use by an infant may include openings which permit the feeding of the infant, wiping of his face and other functions. Medical staff may also need to have quick access to the user's nose or mouth, and it is convenient that this may be accomplished without removal of the mask. Another important aspect which dictates the opening size etc. relates to psychological factors, to minimize the anxiety felt by users. This can be particularly the case with infants, the elderly and those suffering from diminished mental capacity. Thus, a variety of different configurations of the openings is contemplated. The mask has a size and shape so as to provide an oxygen-enriched zone surrounding the user's nose and mouth.

The open structure of the mask body permits the generation of an effective gas plume during use, even with the supply of a relatively wide range of gas deliver rates. The characteristics of the plume are determined at least in part by the configuration of the openings and the webs which define the mask body. The open structure also permits exhaled gases to be easily dissipated. However, unlike a fully open mask, the web-like bridges effectively obstruct at least some of the inflowing ambient air so as to enhance the generation of plume of enriched gas around the user's nose and mouth.

The openings within the mask body can take on any convenient and suitable shape such as square, triangular or rectangular or other polygonal, or round or oval. The openings have a size range of between 0.25 square inches in area and 6.0 square inches and preferably between 0.25 and 3.0 square inches.

The size and shape of the mask is preferably optimized to minimize the surface area of the mask body and maximize the open area so as to enhance the user's comfort. This is accomplished by providing a relatively large area of the mask body being open, for example by providing a plurality of relatively large openings within the body. It has been found that the mask body may comprise a relatively open structure if the gas diffuser mounted to the mask is positioned generally directly opposed to the user's nose and mouth region and spaced apart from the user's face so as to generate a plume of turbulent gas flow which covers the mouth and nose region of the user. In order to generate this plume of turbulent flow, the diffuser comprises a rear wall which fixedly receives a gas delivery tube, the mouth or nozzle of the tube discharging into the interior of the diffuser towards the user's face. A gas flow disrupter is positioned between the nozzle and the user's face.

The rear portion is surrounded by a peripheral wall or flange extending towards the interior of the mask and the user's face so as to form a generally concave structure to assist in directing the gas flow towards the user. Preferably the rear portion is a wall which may be flat or curved, with the gas outlet entering the wall, for example at a generally central location. The peripheral wall may comprise a generally triangular shape as in the above-described embodiment, or any other convenient shape. A turbulent flow pattern is generated by providing one or more obstructions associated with the diffuser in the path of the gas flow after it exits the gas delivery tube. For example, a baffle may be provided within the interior of the diffuser, which may comprise a mushroom-shaped structure which partly obstructs the path of the discharged gas.

The diffuser conforms to dimensional and positional constraints in order to provide a gas plume having sufficient size to substantially cover the user's nose and mouth. It has been found that the diffuser should comprise a width of no more than 40 mm at its widest point and a maximum height of 80 mm and preferably smaller than this in both dimensions. The diffuser is positioned within the mask such that no part of the diffuser is outside of a region defined in relation to a point between the base of the user's nose and his upper lip, the region comprising a space 40 mm above and below this point in the vertical plane when the mask is vertical and 20 mm on either side of this point in the side-to-side direction. Preferably the diffuser is centered in side to side and vertical dimensions relative to this point. Further, the diffuser is preferably mounted so as to leave a gap between the diffuser and the user's face of between 12 and 40 mm as measured from the user's skin surface between upper lip and nose. Preferably, the diffuser is generally triangular in shape with base downwardly, and preferably the width and height are between 20-30 mm and 17-27 mm respectively.

It has been found that a mask which is provided with a diffuser that conforms to the dimensional requirements described above, and which is positioned within the mask as described, and wherein the mask body includes a plurality of openings or cut-outs, provides an optimal level of comfort, with minimal coverage of the face while still permitting an oxygen-enriched zone fully covering the user's nose and mouth. Preferably the cut-outs within the mask body should comprise at least 30 percent of the total surface area of the body when measured as if the body were considered to comprise a plane surface, and still more preferably the cut-outs comprise between 30 and 80 percent of the total surface area. In a still more preferred version the range is more narrowly defined as being between 50 and 80 percent, and yet more narrowly as between 60 and 75 percent.

An oxygen delivery mask permits an efficient delivery of oxygen-enriched gas in a comfortable fashion if it includes a combination of an oxygen diffuser opposed to the user's nose and mouth region and directed so as to direct a turbulent gas plume directly at the nose and mouth, and at least one opening within the mask body. Without intending to be restricted to a theory, it is believed that the user's breath inspiration generates negative pressure within the mask interior thereby creating a mixing effect whereby exterior air is drawn through the mask openings into the turbulent gas plume via a venturi effect. Upon exhaling, a positive pressure is generated within the mask and the exhaled air is exhausted through the openings. This maintains within the mask interior an oxygen-rich and $CO_2$-poor environment, which enhances the user's comfort level and is more medically effective.

Positioning of the diffuser opposed to the nose and mouth region so as to direct a turbulent plume directly towards the user's nose and mouth also permits an oxygen-enriched gas plume which is of generally equal gas makeup over both the mouth and nose. Thus, user inhales the same gas mixture whether breathing through mouth or nose. The diffuser is suitable shaped and positioned so as to cover both the nose and mouth of a typical user.

Preferably the mask body is semi-rigid, for example fabricated from a molded plastic such as PVC, ABS, polypropylene, silicone polycarbonate or other suitable inert resilient material. The mask body is thus able to retain its shape when in use and to maintain the diffuser in its appropriate position, but being flexible for patient comfort and also to permit the mask to be flattened for storage, transport and the like. The ribs described above associated with the webs assist the flattened mask to spring back into shape when released.

The oxygen delivery mask of the present invention provides an easy to use, comfortable, reliable and efficient mask for delivery of oxygen to a patient. As well, since this mask construction does not provide complete enclosure over the patient's nose and mouth, there is less chance of claustrophobia.

In a further aspect, although the invention has been described for use for delivering oxygen or an oxygen-enriched gas it will be seen that with modifications it may be used for other medical applications such as delivery of anesthetic or other gases to a patient.

According to a first broad aspect there is disclosed a facial mask for delivery of a gas to the nose and mouth region of a patient, comprising an at least partially rigid mask body having a rim for contacting the patient's face substantially covering the nose and mouth of the patient, means to engage the mask to a patient so as to maintain contact between the user's face and said rim, a central portion, a connection to a supply of gas, a gas nozzle opening into the interior of said mask at said central portion operatively connected to said gas connection, a diffuser at least party surrounding said nozzle and fastened to and supported by said mask body at a position spaced apart from and not contacting the user's face, said diffuser including a tubular wall structure extending from said central portion towards said patient's face, and a gas flow disrupter fixed in position between said nozzle and said user's face so as to allow gas flow while generating a turbulent plume of said gas at the user's nose and mouth, said mask body further comprising an array of elongate webs between said rim and said central portion, said webs defining a plurality of openings therebetween within said body to permit access to the user's face from the outside of said mask.

According to a second broad aspect there is disclosed a facial mask for delivery of a gas to the nose and mouth region of a patient, comprising an at least partially rigid mask body having a rim for contacting the patient's face substantially covering the nose and mouth of the patient, said mask body having a generally open structure having a plurality of openings permitting communication between the interior and exterior of said mask, fastening means to engage the mask to a patient so as to maintain contact between the user's face and said rim, a connection to a supply of gas, a gas nozzle opening into the interior of said mask operatively connected to said gas connection, a diffuser at least partly surrounding said nozzle and fastened to and supported by said mask body at a position spaced apart from and not contacting the user's face, said diffuser being positioned generally centrally within said mask and including a gas outlet nozzle, a gas flow disrupter fixed in position between said nozzle and said user's face so as to allow gas flow while generating a turbulent plume of said gas substantially at a non-oblique angle towards the user's nose and mouth and a peripheral flange surrounding said nozzle, said diffuser being positioned within said mask so as to fit entirely within a space defined in relation to a point on the user's face about halfway between the base of the nose and uppermost edge of upper lip, said space defined in the vertical plane as 40 mm above and below said point, 20 mm on either side of said point and horizontally spaced apart from said point by between 12 and 40 mm when said user is upright.

According to a third broad aspect there is disclosed a facial mask for the delivery of a gas to the nose and mouth region of a patient, comprising a resilient mask body having a rim for contacting the patient's face surrounding the nose and mouth of the patient, a gas nozzle opening into the interior of said mask operatively connected to a gas connection, a central region of said mask body for supporting said gas nozzle, and an array of elongate webs joining said central portion to said rim to form a concave structure defined by openings between said webs, wherein said openings comprise at least 30% of the surface area of said mask body, each of said webs comprising a substantially elongate member radiating outwardly from said central region, each of said webs having inside and outside surface, at least some of said webs including a stiffening rib on said inside surface protruding towards the user's face when worn, said rib extending longitudinally substantially the length of said web for increasing the structural rigidity of said mask body, said web and integral ribs being of a suitably resilient material to permit said mask to be flattened during storage or transport, and resiliently resume a suitable concave shape upon release.

According to a fourth broad aspect there is disclosed a facial mask for delivery of a gas to the nose and mouth region of a patient, comprising an at least partially rigid mask body having a generally concave shape, said body comprising a rim for contacting the patient's face surrounding the nose and mouth of the patient, a central region, and an array of elongate web-like bridging portions between said central region, and an array of elongate web-like bridging portions between said central region, and said rim to define a concave mask body, with spaces between said webs defining openings such that at least 30% of the surface area of said mask body is open, said mask further comprising a connection for a supply of gas, a gas nozzle opening into the interior of said mask operatively connected to said gas connection, and a diffuser at least partially surrounding said nozzle and comprising a diffuser wall having a base joining with said central region and an upper edge facing said user, said diffuser extending towards the user's face, said diffuser having a gas flow disrupted fixed in position between said nozzle and said user's face so as to allow gas flow while generating a turbulent plume of gas towards said user's face, the wall of said diffuser having a height of between 6 and 25 mm from the base to exposed edge thereof.

BRIEF DESCRIPTION OF THE DRAWINGS

These and other advantages of the invention will become apparent upon reading the following detailed description and upon referring to the drawings in which.

Figure 1:
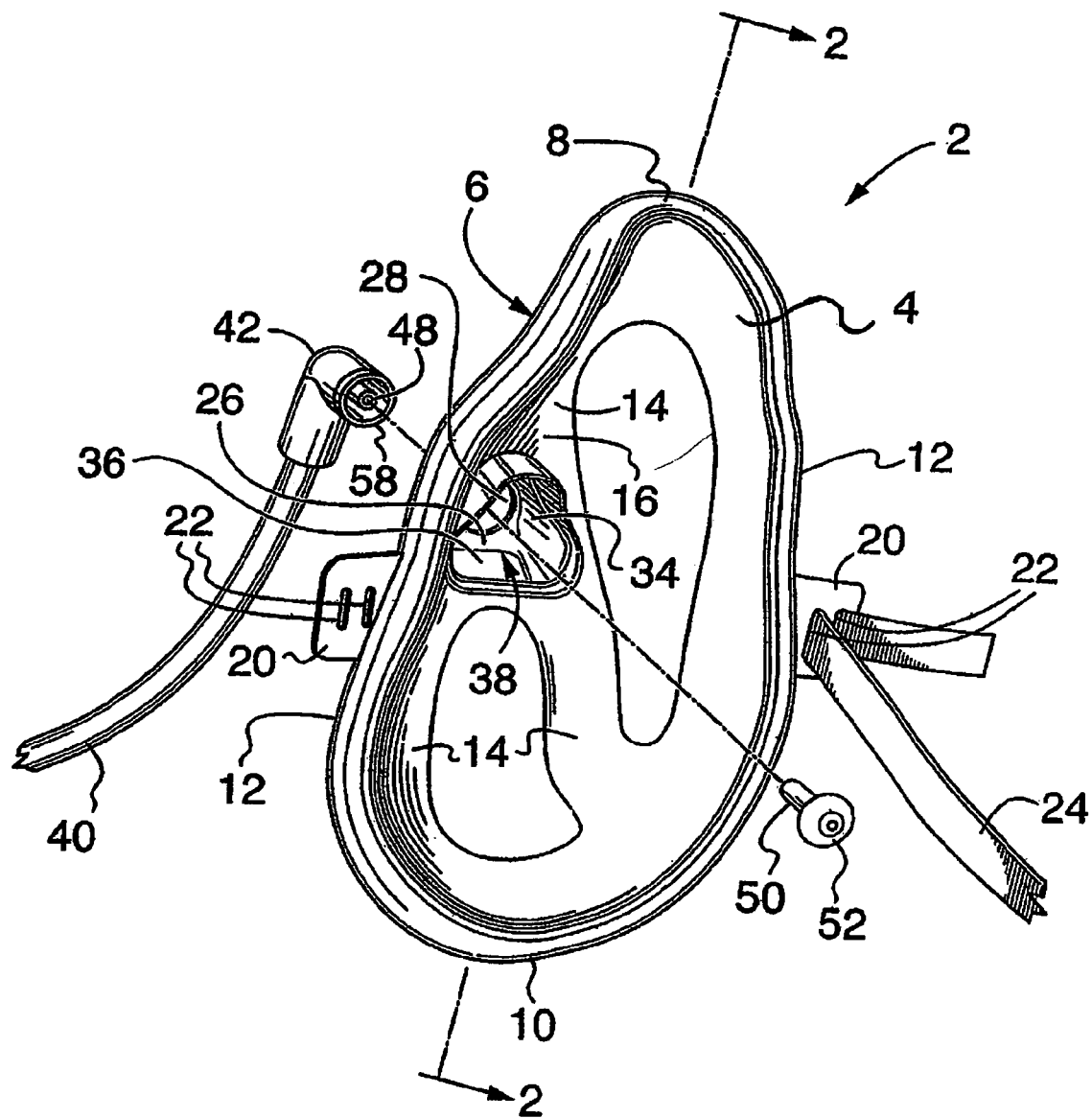
FIG. 1 is an exploded perspective view from the rear of one embodiment of the oxygen delivery mask according to the present invention.

While the invention will be described in conjunction with illustrated embodiments, it will be understood that it is not intended to limit the invention to such embodiments. On the contrary, it is intended to cover all alternatives, modifications and equivalents as may be included within the spirit and scope of the invention as defined by the specification as a whole including the appended claims. It will be understood that dimensions and relative dimensions described and illustrated herein are intended to be by way of example only of specific embodiments and unless otherwise indicated are not intended to limit the scope of the invention. References herein within both the description and claims to specific directions and positions such as "horizontal", "vertical", "forward" and the like are intended only to provide a convenient means of description and are intended to be in reference to the mask in an upright forward-facing position, as if it were worn by a patient in a standing position. Naturally, the mask may be used with the patient in any position.

DETAILED DESCRIPTION

In the following description similar features in the drawings have been given similar reference numerals.

Figure 2:
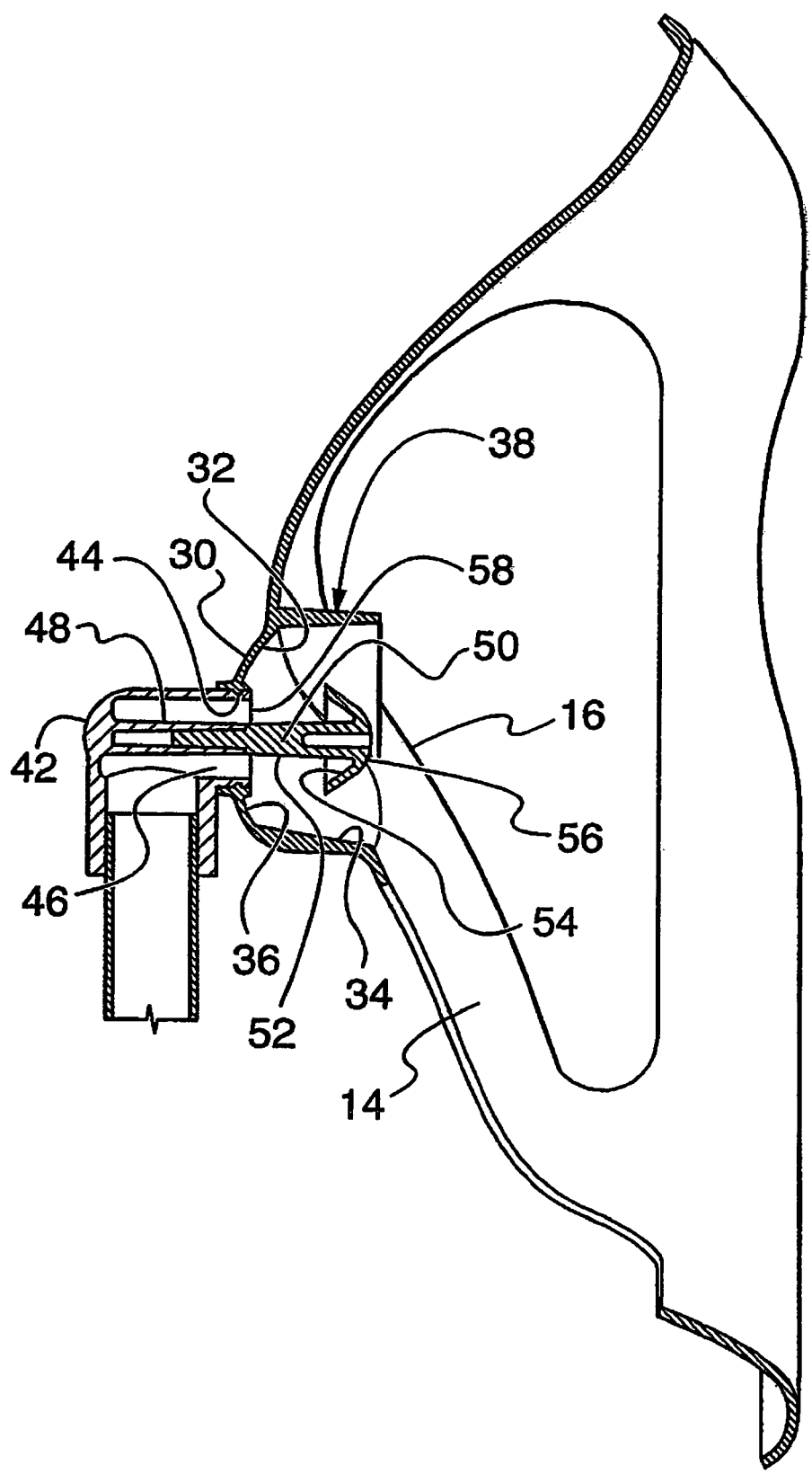
FIG. 2 is an elevational section view of the mask of FIG. 1, along lines 2-2 of FIG. 1.
Figure 3:
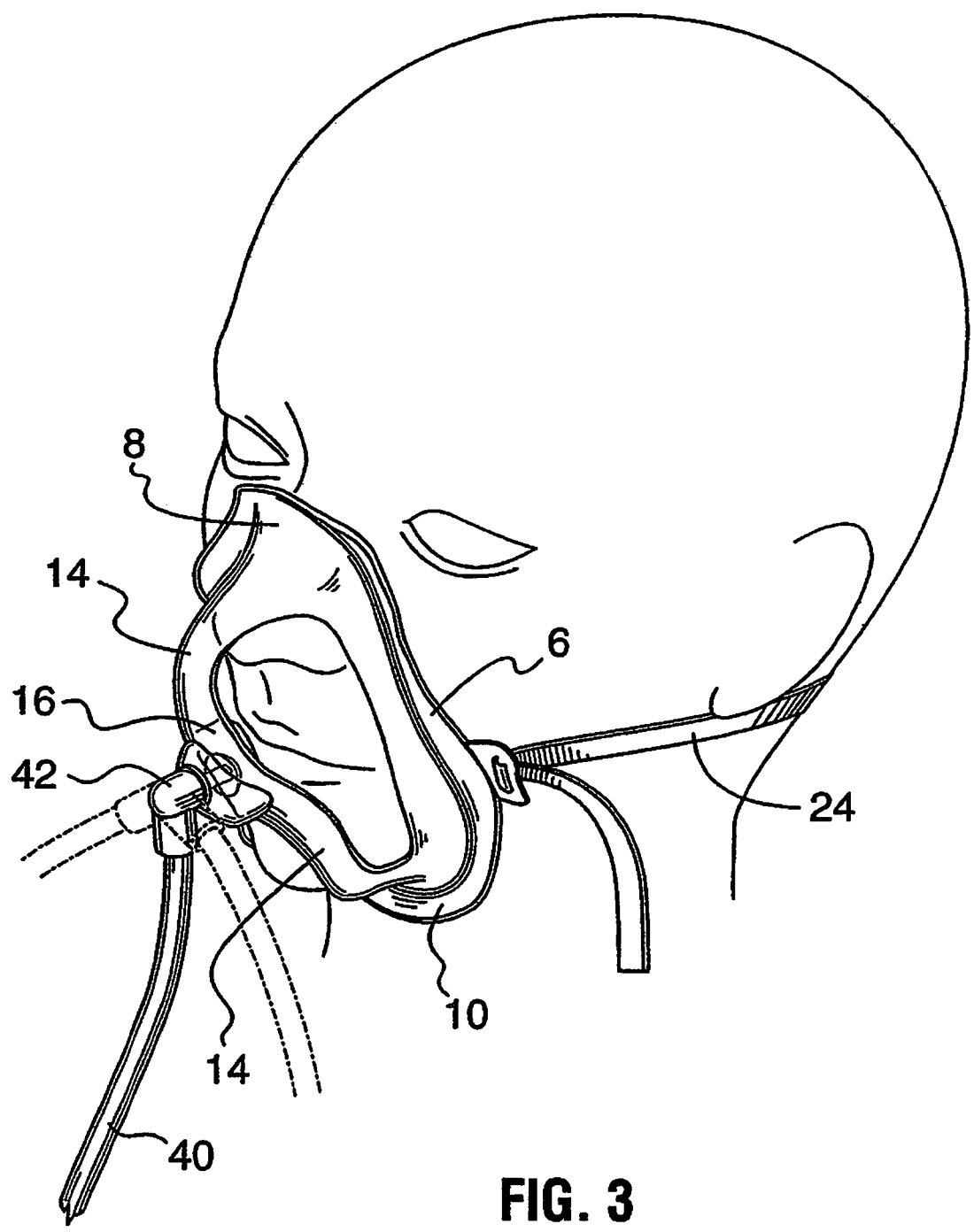
FIG. 3 is a perspective view from the front of the mask of FIG. 1.

Turning to FIGS. 1 and 2 there is illustrated an oxygen delivery mask 2 in accordance with the present invention. Mask 2 is made up of a body 4 having a peripheral portion 6 with a top 8 and a bottom 10. Sides 12 extend between top 8 and bottom 10. As can be seen in FIG. 3, peripheral portion 6, when mask 2 is in use, rests on portions of a user's face both above the user's nose (top 8) and on the user's chin (bottom 10). Integrally formed with peripheral portion 6 are bridge portions 14 which integrally connect with a central portion 16. Bridge portions 14 and central portion 16 have an inverted "Y" shaped configuration (from top to bottom of the mask), when viewed from the front (FIG. 5), providing unobstructed access to and viewing of the patient's mouth and other parts of the patient's face, so that for example, the patient may eat and drink without removing the mask. Of course other configurations of bridge portions may be provided as desired or appropriate, such as, for example, an "X" shape, a "+" shape or "T" shape. Peripheral portion 6, bridge portions 14 and central portion 16 are preferably made of a fairly soft, semi rigid plastic material. The term "semi-rigid" refers to a material that is generally resilient but which provides sufficient rigidity to substantially maintain its shape when in normal use. The bridge portions 14 thus have sufficient rigidity to retain the diffuser 38, discussed below, in position. Suitable materials for the peripheral, bridge and central portions 6, 14 and 16 include plastics such as PVC, Silicone, Foam, Polystyrene and any other thermoplastic elastomers Tabs 20 extend outwardly from sides 12, and are provided with, for example, slots 22 in which may be adjustably secured ends of an elastic strap 24 for releasably securing the mask 2 in position on a user's face (FIG. 3). As will be understood from FIGS. 1 and 3, peripheral portion 6, bridge portions 14 and central portion 16 are contoured so as to rise from base 26 of peripheral portion 16 in a curved contour so that central portion 16 sits spaced over the nose and mouth of the patient when the mask 2 is in position. A circular aperture 28 extends through central portion 16 from outer surface 30 to inner surface 32.

Integrally formed on inner surface 32 of central portion 16, is a triangular wall 34, extending about a base 36 which circumscribes circular aperture 28. This wall 34 and base 36 together form a shape which is of generally concave configuration, with one of the apexes of the triangle formed by wall 34 being oriented towards top 8 of mask 2 and the other two apexes oriented towards bottom 10. Thus, a generally triangular shape is formed by the mask, albeit generally with rounded corners, which approximates the human nose and mouth region, so as to generate an oxygen enriched region within the mask which substantially covers the user's nose and mouth. This wall and base form a diffuser 38 in which the wall 34 includes an upper wall portion and a lower wall portion. As best seen in FIG. 2, the end of the lower wall portion 36 is continuously formed with the mask body. The diffuser has a similar function to the diffuser construction described and illustrated in applicant's earlier patents and applications referred to previously herein. The diffuser 38 has a maximum width of about 25 mm and a maximum height of about 22 mm.

Figure 5:
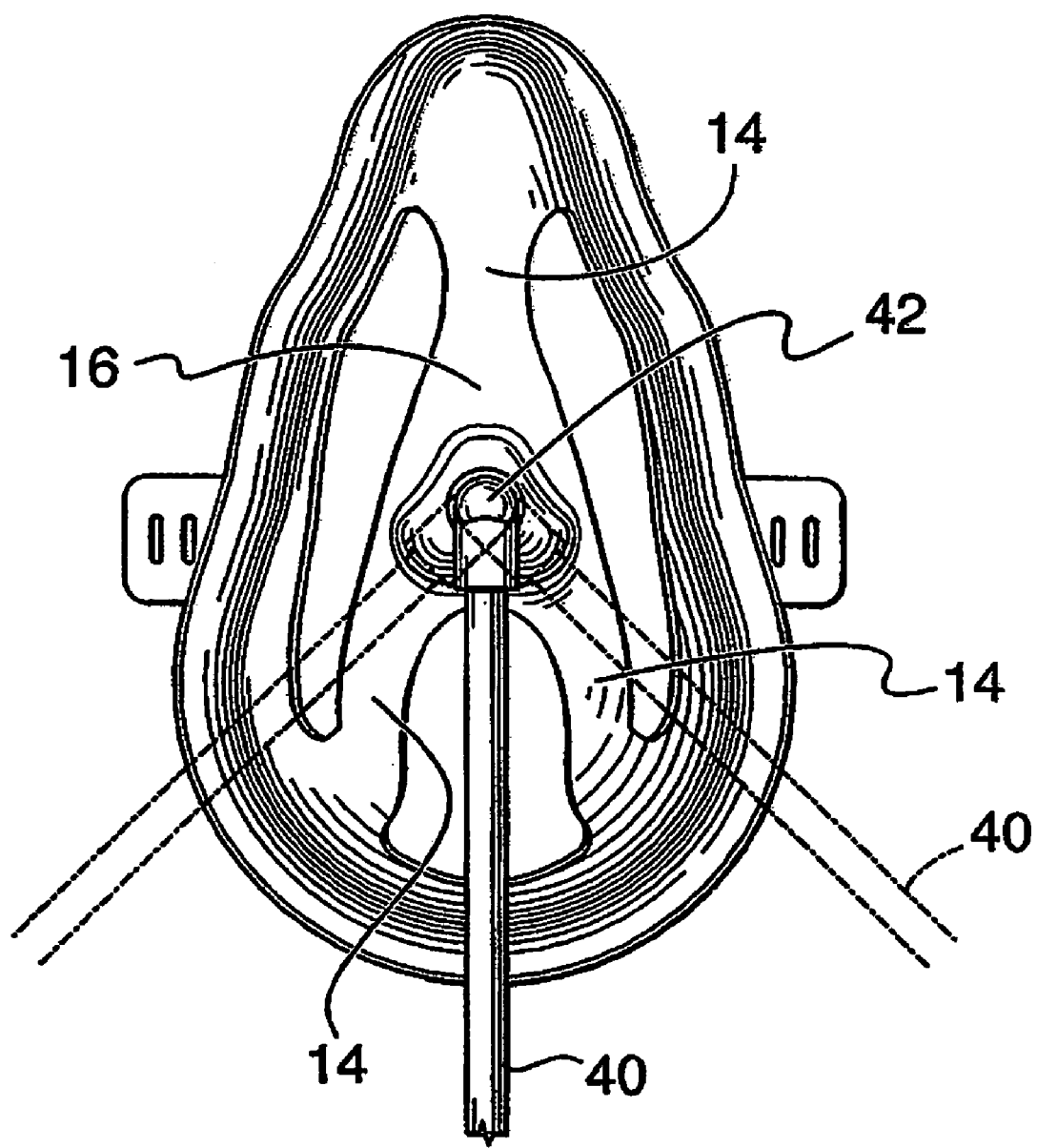
FIG. 5 is a front elevation view of the mask of FIG. 1.

In the embodiment of mask illustrated in FIGS. 1 to 3, an oxygen delivery tube 40 is secured in a rigid elbow 42, elbow 42 being rotatably secured by an appropriate, conventional securing means such as frictional engagement in aperture 28 or its snapping into an undercut 44 about aperture 28 on the outer surface 30, so that it can pivot about the circumference of aperture 28 (FIGS. 3 and 5). Elbow 42 provides a passageway 46 for delivery of oxygen, during operation of the device, into diffuser 38 on the inner surface 32 of central portion 16. The diffuser 38 and associated baffle are shaped so as to generate a plume of turbulent flow of oxygen-enriched gas which surrounds the user's nose and preferably also his mouth. The generation of this plume requires a suitable discharge velocity of gas through the nozzle This may be accomplished by providing a gas discharge rate between 1-15 Liters/min) Formation of the plume is related to the physical design of the nozzle, diffuser and baffle. The blending of the oxygen and atmospheric oxygen is related to the gas velocity. Without wishing to be tied to any particular theory of operation, the physical properties of the divide required to generate a plume include the shape, size and positioning of the baffle which serves to deflecting the gas flow back down, then bounce of sidwalls to create this plume-so the walls would have to be no closer then half the diameter of the pin top. The direction of the gas flow exiting the diffuser is substantially directly towards the user's face so as to strike the user at an angle generally perpendicular to the user's face. The gas flow is thus non-oblique in relation to the user's face. The diffuser 38 is positioned so as to direct the flow most strongly at the user's nose and mouth region. It has been found that the configuration described herein efficiently provides an oxygen-enriched zone in the region surrounding the user's mouth and nose, while permitting relatively large cut-outs within the mask.

The baffle 50 is positioned within the path of the gas exiting the nozzle and has a shape and size which is suitable for interrupting the linear gas flow exiting the nozzle so as to generate turbulence. It will be seen that a variety of sizes and shapes will achieve this function. In the illustrated example, the baffle comprises an upstanding stem 48 within elbow 42 which provides a means for releasable attachment thereto of post 50 of mushroom shaped baffle 52. As can be seen in FIG. 2, the inner end of baffle 52 has a curled back conical lip 54 on its head 56, the underside of this lip being in line with oxygen passing from aperture 26 at the inner end 58 of elbow 42. This curled back conical lip 54 is of a size and configuration, with respect to wall 34 of diffuser 38, such that turbulence is generated in the stream of oxygen passing from elbow inner end 58 and aperture 28, creating a plume of oxygen enriched air at the patient's nose and mouth when the mask is in position.

Figure 4:
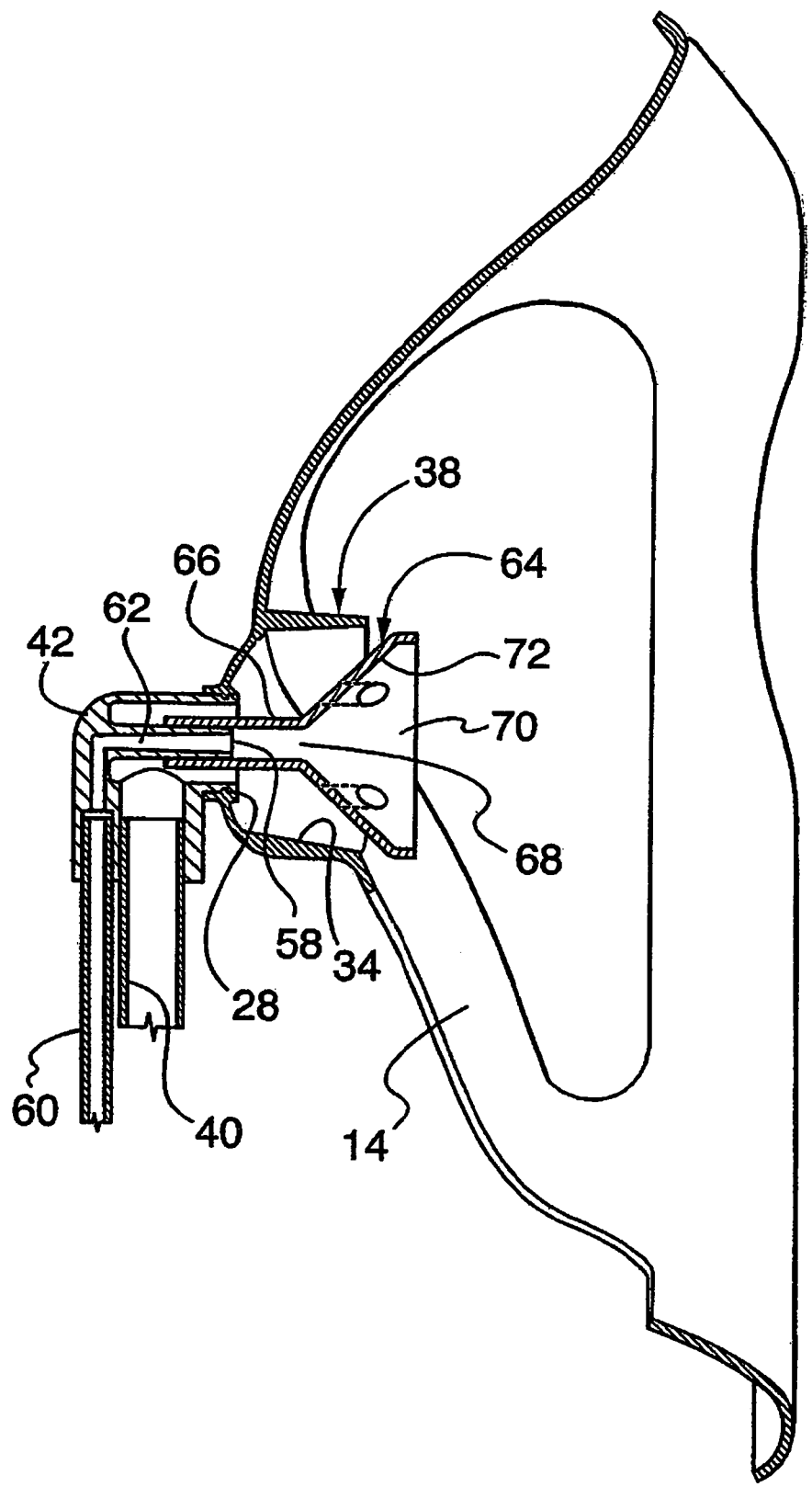
FIG. 4 is an elevational section view of a second embodiment of an oxygen delivery mask in accordance with the present invention, including a carbon dioxide monitoring function.

In the alternative embodiment of mask 2 illustrated in FIG. 4, while mask body 4 and integral diffuser 38 are of a similar configuration to those of FIGS. 1, 2 and 3, in addition to an oxygen delivery tube 40 passing into elbow 42, elbow 42 is configured to have an oxygen/carbon dioxide monitor tube 60 secured to it, which tube communicates with a separate oxygen/carbon dioxide monitor passageway 62 extending within elbow 42 to its inner end 58. Oxygen/carbon dioxide monitor tube 60 and passageway 62 are separate and independent from oxygen delivery tube 40 and oxygen delivery passageway 46. Oxygen from delivery tube 40 is again delivered through elbow 42 to aperture 28 and the inside of mask 2 and the wall 34 of diffuser 38 circumscribes this aperture 28 and directs the flow of oxygen generally outwardly from diffuser 38.

In this embodiment, baffle 64 has a hollow post 66, the hollow center communicating with an opening 68 on the inside of baffle 64, and with the oxygen/carbon dioxide monitor passageway 62 and tube 60.

Head 70 of the baffle 64 circumscribes the opening 68, the head being of a concave shape formed by wall 72. This head 70 fills a significant part of the interior of diffuser 38. Wall 72 extends outwardly beyond the edges of wall 34, and generates the necessary oxygen turbulence to provide an effective plume of oxygen for delivery to the nose and mouth area of the patient when the mask 2 is in position. At the same time however, an effective oxygen/carbon dioxide monitoring of the patient's exhaled breath is permitted through the oxygen/carbon dioxide monitor opening 68 within head 70.

Figure 6A:
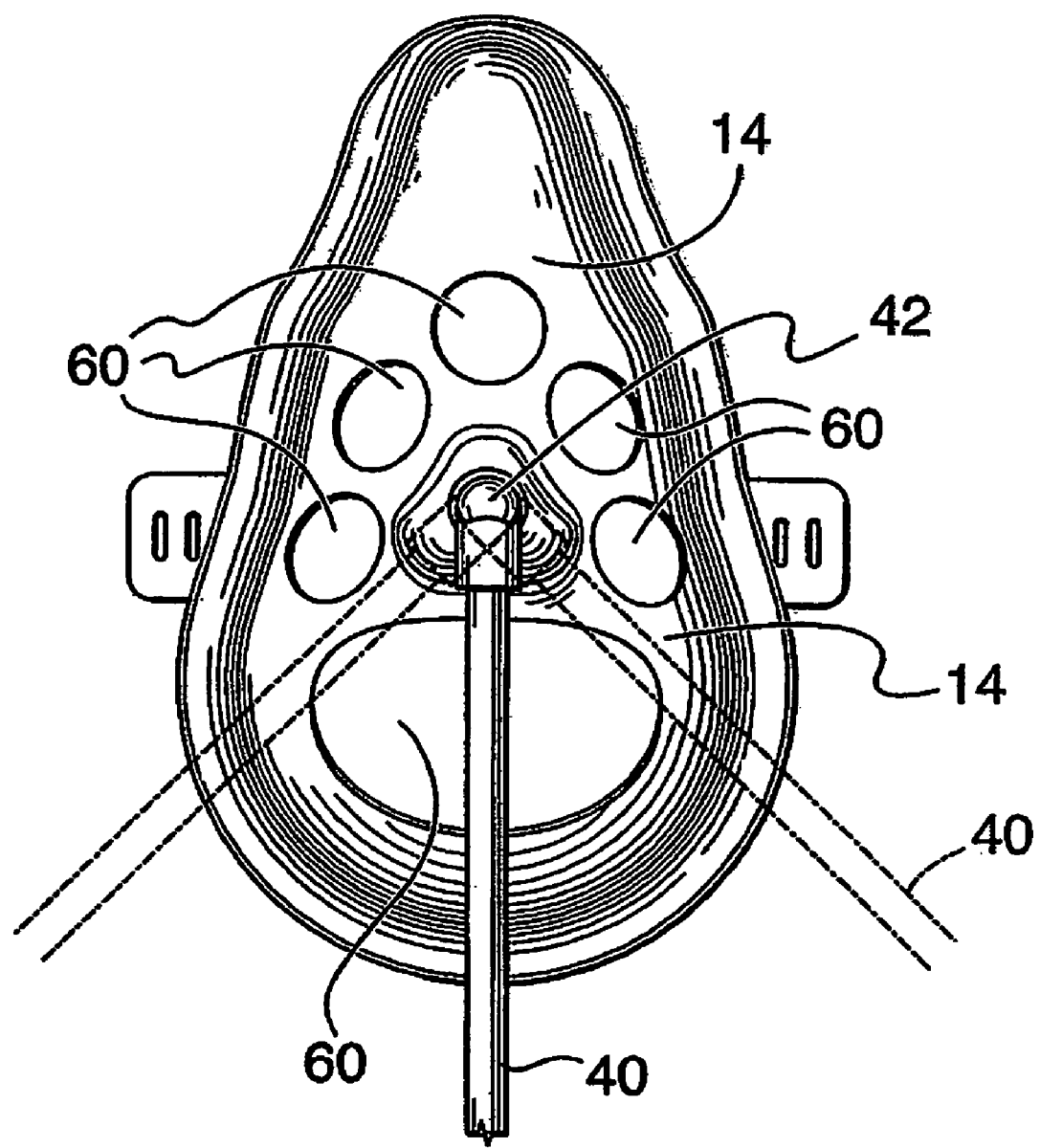
FIGS. 6A, 6B and 6C are front elevational views of further alternative embodiments of the mask.
Figure 6B:
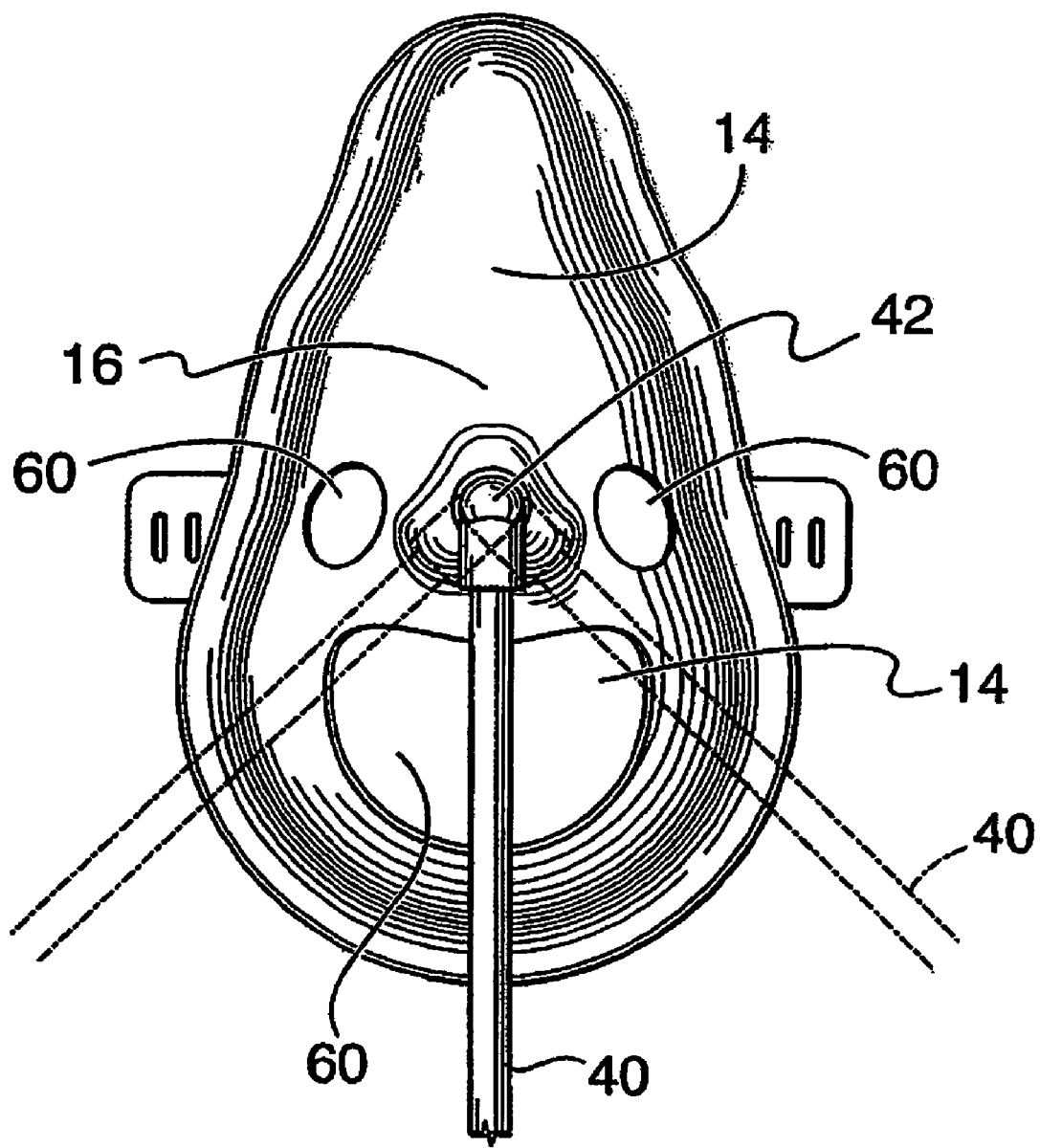
Figure 6C:
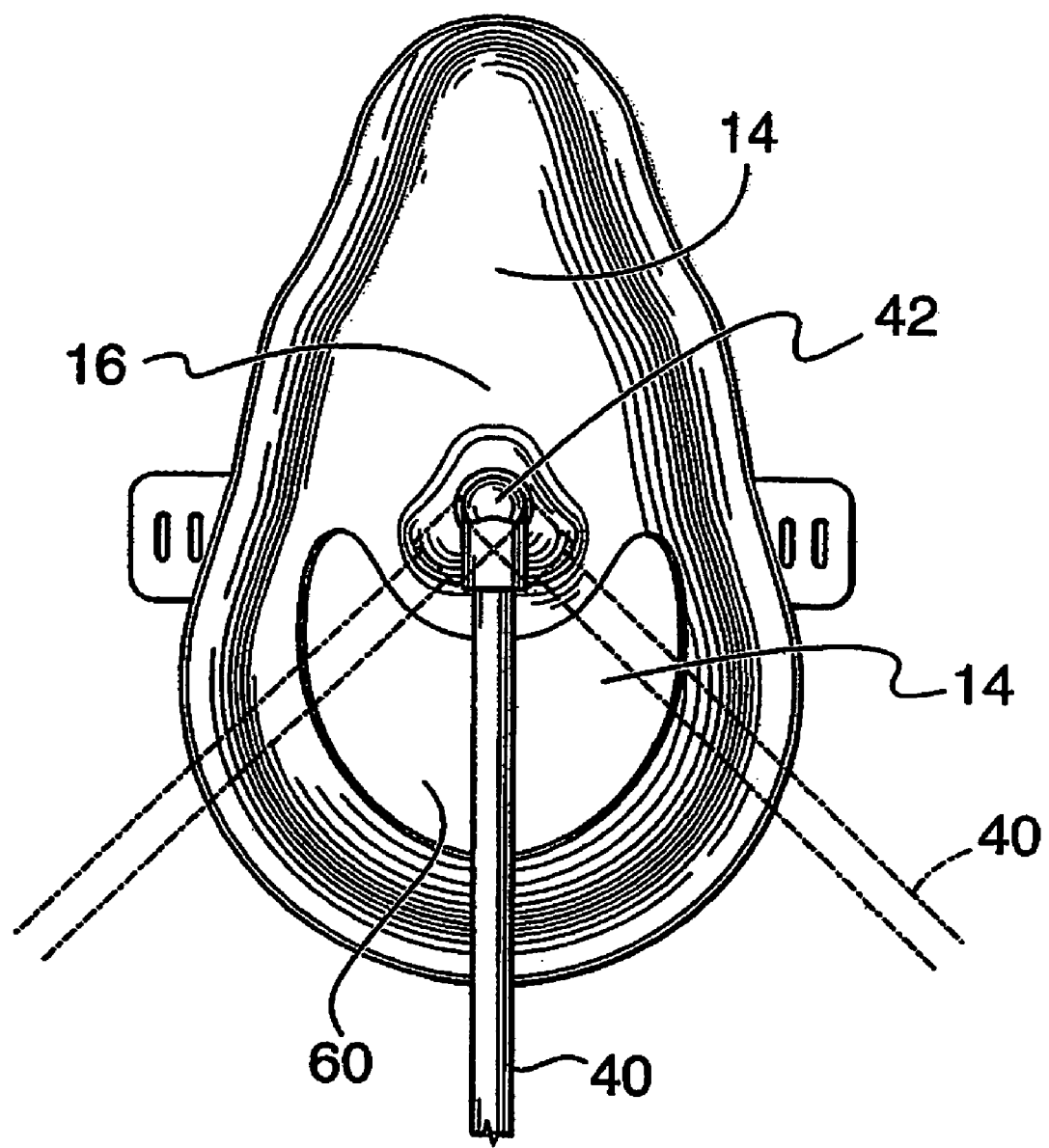

In further embodiments shown in FIGS. 6A, 6B and 6C, a mask 2 comprises a body 4 having a peripheral rim 6. The rim 6 comprises a material such as PVC or Silicone which provides sufficient rigidity to permit the mask to maintain its shape while permitting a degree of resiliency to permit the mask to comfortably conform to a user's face. The rim is provided with an outer surface for contacting the user's face of a material which is soft and pliable plastic with a Durometer range of 20-100 Shore A. The rim preferably has a roughly triangular shape to generally conform to a human nose and mouth region, namely a broad base and a narrow apex, with rounded corners. The rim 6 may alternatively comprise a bendable material such as aluminum which retains its shape when flexed, which may be provided to the user in a shape which roughly follows the contours of a typical human face. The mask may be provided in a plurality of rim sizes to fit different classes of users, for example infants and small, medium and large adults.

The body 4 comprises a web of shaped substantially rigid material. This may comprise a semi-rigid material such as that described above in connection with the first embodiment. However, if the body 4 is provided with a more lace-like structure defined by a large number of cut-outs, described below, a more rigid material will be desired such as TPE- "thermoplastic elastomer". In general, the body has sufficient rigidity to maintain its generally cup-like configuration and to support the diffuser 38 which is fastened to and supported by the body, at a position spaced apart from the user's face. Because the relative position of the diffuser 38 is important to the functioning of this version, the body should have sufficient rigidity to maintain the central position of the diffuser 38 during normal use of the mask. The body 4 may possess a degree of resiliency to enhance user comfort and daily functions and to permit the mask to better conform to the user's face. The body comprises a plurality of cut-outs 60 which may be of any shape and size suitable to serve several desired functions. These functions include permitting the user to speak, eat and drink with a minimum of obstruction, wipe or blow his nose, scratch or otherwise touch his face, kiss and other normal activities. As well, it is contemplated that others such as health professionals may rely on the cut-outs 60 to feed or provide fluid to the user or for other functions. Thus, it is contemplated that relatively large openings are provided in the region of the user's nose and mouth. However, other arrangements of openings are possible such a larger number of smaller openings. The openings must not be so many or large as limit the ability of the web to fixedly support the diffuser 38.

The diffuser 38 is mounted within the mask body 4 so as to be centered vertically and horizontally (side-to-side) above a point which when the mask is worn by a person, is about halfway between the base of the nose and the upper lip.

Preferably, the cut-outs 60 comprise at least 50 percent of the total surface area of the body 6 (when measured with the surface area including both open and closed areas) and still more preferably the cut-outs comprise between 50 and 80 percent of the total surface area. In a still more preferred version the range is more narrowly defined as being between 60 and 75 percent.

The diffuser 38 protrudes through and is supported by the body 4 at a position generally opposed to the user's nose and mouth region. The diffuser and associated baffle are substantially as described in connection with the embodiments. However, it has been found that if the diffuser body conforms to particular size and positioning limits, it effectively generates a zone or region of oxygen-enriched gas in the region of the patient's nose and mouth, regardless of the number, size and shape of the cut-outs 60. For this purpose it is desirable to fabricate the body 4 from a relatively rigid material such as polystyrene, thermoplastic elastomer or polycarbonate. The diffuser 38 receives a gas supply from supply line 40, via elbow 42 in the same manner as described above. A mushroom-shaped baffle within the interior of the diffuser 38 assists in the dispersal of gas. It will be further apparent to those skilled in the art that the diffuser 38 may comprise a range of sizes and shapes. However, in order to generate the desired region of oxygen enriched gas the diffuser comprises a cup-like body opening towards the user. It should have a maximum size and positioning within the mask that permits the diffuser to fit entirely within a region of the mask defined by reference to an imaginary point on the user's face between the base of the nose and upper lip, in the midline of the face, with the diffuser entirely fitting within the space defined by 20 mm on either side of this line horizontally and 40 mm above and below the this point vertically (when the user is upright). Preferably the diffuser is sufficiently small so as to permit some slippage of the mask while still remaining within this region, for example as described above a generally triangular configuration about 25 mm wide at its base and about 22 mm high. The diffuser is also positioned within the mask such that the gas discharge nozzle is between 12 and 40 mm displaced forwardly of the user's face measured from the area between the upper lip and below the nose of a users face. The body 6 must have sufficient forward protrusion so as to position the rear rim of the diffuser so that it does not contact the nose of the typical user. The spacing thus required will vary somewhat with different sizes of masks. For example, the diffuser may protrude rearwardly into the interior of the body 4 by about 2 mm, and the body thus has an overall depth of about 15 mm.

According to another embodiment, illustrated in FIGS. 7 and 8, the mask body 4 is similar in overall configuration to the embodiments described previously, including a rim 6 for contacting the patient's face, a central diffuser structure 34 spaced apart from the user's face, and an array of web-like bridges 102, 110 and 112, described below, radiating outwardly from the central portion 16 to join the central portion 16 to the rim 6. The bridges have a generally curved shape so as to define the concave structure of the mask body 4. The bridges define a generally open structure to the mask body, including preferably a relatively large opening 100 in the central lower region approximately opposite to the patient's mouth. The bridges include first and second opposing lateral bridges 102, which when the mask is upright radiate outwardly in a substantially horizontal direction, on either opposing side of the central region. The horizontal bridges 102 define upper and lower lateral openings 106, 108 within the mask body. Preferably, the bridges further include opposing downwardly angling bridges 110, with the space 100 therebetween defining the central lowermost opening facing the user's mouth. The remaining bridge 112 extends vertically upwardly between the central portion 16 and the rim 6.

Within the present example, the lateral bridges 102 have curved side edges 114, such that these bridges 102 are at their narrowest in the central portions thereof, tapering outwardly towards either end in a symmetric fashion. The approximate width of each bridge 102 at its narrowest is 11 mm. The central vertical bridge 112 is approximately 7 mm at its narrowest, and the opposing left and right lower bridges 110 are approximately 11 mm wide.

The central diffuser structure includes an oxygen inlet 116 with a mushroom-shaped baffle (as shown in FIG. 2 and here removed for clarity) partially obstructing the inlet 116 to generate a turbulent gas plume. The baffle is surrounded by the wall 34 extending horizontally towards the user's face, when the mask is upright, with the wall having a generally triangular shape when viewed in front elevation from the perspective of the user. The diffuser region defined by the height of the wall from its base to its top (referenced now to the mask being horizontal) is deeper than in the embodiments described above so as to extend closer to the user's face. In the previous embodiments described above, the wall ranges from being generally flush with the central part of the mask body, to an outward protrusion of about 12 mm. In this embodiment, the wall has a minimum protrusion of about 13 mm and a maximum protrusion of about 20 mm. It is contemplated that these may range plus or minus by about 5 mm. As is seen in the Figures, the wall varies in protrusion to accommodate the inward and upward tilt of the mask, such that the expose rim of the wall is generally vertical when the mask is upright. As well, the exposed rim 117 is angled such that it protrudes more towards the user at its upper region relative to its lower region. For example, the rim may have a generally curvilinear shape as see in the Figures, such that when seen from the side, the rim has in general a backwards "S" shape.

The embodiment further includes an array of stiffening ribs 120, which are integral with the webs, and serve to stiffen the webs for maintaining their shape with the use of relatively thinner material. The ribs 120 extend longitudinally substantially the length of each web 102, 110, 112, and extend approximately centrally along the interior of each web. The ribs 120 are tapered, such that their tallest portion joins with the wall of the diffuser, tapering to a minimal height adjacent the rim. Preferably, the ribs and webs are molded together and comprise the same material, which preferably is resilient. As described above, the mask is preferably molded or otherwise formed from a suitably resilient material, such that the mask may be stored in a substantially flattened position, and when released the ribs assist the mask to snap back into their concave position suitable for patient use.

In a further aspect, the mask rim 6 comprises an array of attachments for attaching different selected straps, bands, or the like for fastening the mask to the user's head. Thus, the rim includes opposing outwardly extending tabs 124, each of which includes an opening 126 for fastening a band or the like. The tabs 124 preferably are positioned at about the middle region of the mask. Additional openings 128, 130 are provided through the rim 6, including opposed openings 128 slightly above the tabs and two opposed openings 130 below the tabs, near the lower end of the mask. A single band (not shown) may be fastened to the tabs, and/or the openings slightly above the tabs, for extending around the back of the user's head. Alternatively, a pair of opposing looped fastenings (not shown) may be attached on either side of the mask, with a first end of the loop attaching to the tab and the second end of the loop attaching to the lower opening. The loops are preferably elasticized for extending around the user's ears, as a convenient way to hold the mask snuggly against the user's face, without the need for a band extending fully around the backside of the user's head.

It has been found that masks within the scope of the present invention, and in particular the final embodiment described herein, are acceptable with a relatively high oxygen flow rate, with relatively high oxygen concentrations within the mask interior.

In a study, a mask according to the last embodiment described above was tested using live participants with a range of oxygen flow rates. The dilution rate X of the gas plume within the mask was determined according to the following equations:

$$V2 = V1 * d_1^2/d_2^2 = V_3 \text{ (Concentration of Mass, Continuity)}$$

$$X \approx Q/2\pi KV_2 Rr^2 \exp(-2r^2/2Rr^2) \text{ (Concentration of Mass, Gaussian Model)}$$

The sampling tube for the monitor was taped at the same location on all participants, at the center of the lower lip area. Oxygen flow rates were adjusted from 1.5 LPM to 30 LPM. In the experiment, the participants were seated upright in order to simulate field conditions.

A Datex-Ohmeda AS/5 multigas monitor had a sampling flow rate of 200 mL/min, and a delay time of approx. 2.5 s with this configuration. Alveolar gas equilibrium was achieved before stabilized waveforms were noted.

Reported mean oxygen concentrations and associated standard deviations (SD) in the individuals are the results of at least 5 individual readings collected over 90 sec. Intervals. Oxygen was supplied to the participants at 1.5, 2, 2.5, 3, 5, 10, 15, 20, 25 and 30 Liters per minute (LPM). Flow rates were recorded as indicated by the Chemetron 09990-62050 oxygen regulator needle valve. No attempt was made to accurately determine flow rates, since this device is typical to those used in the field.

A measurement was taken from the edge of the diffuser to the participant's lips, in mm. These to later verify for the CFD study and establish the constant (K).

By comparing the published existing Oxygen Flow Setting Table (Table 1) to the newly designed mask (Table 2) the results indicate significant oxygen concentrations at higher flow rate settings.

TABLE 1

| Flow (Liters/min) | O2 Concentration (%) |
| --- | --- |
| 2 | 28-31 |
| 4 | 32-35 |
| 6 | 36-39 |
| 8 | 40-43 |
| 10 | 42-47 |
| 12-15 | 48-50 |

TABLE 2

| Flow (Liters/min) | O2 Concentration (%) |
| --- | --- |
| 1.5 LPM | 21%-35% |
| 2 LPM | 23%-47% |
| 2.5 LPM | 26%-63% |
| 3.0 LPM | 29%-68% |
| 5.0 LPM | 41%-84% |
| 10 LPM | 57%-88% |
| 15 LPM | 64%-90% |

Figure 7:
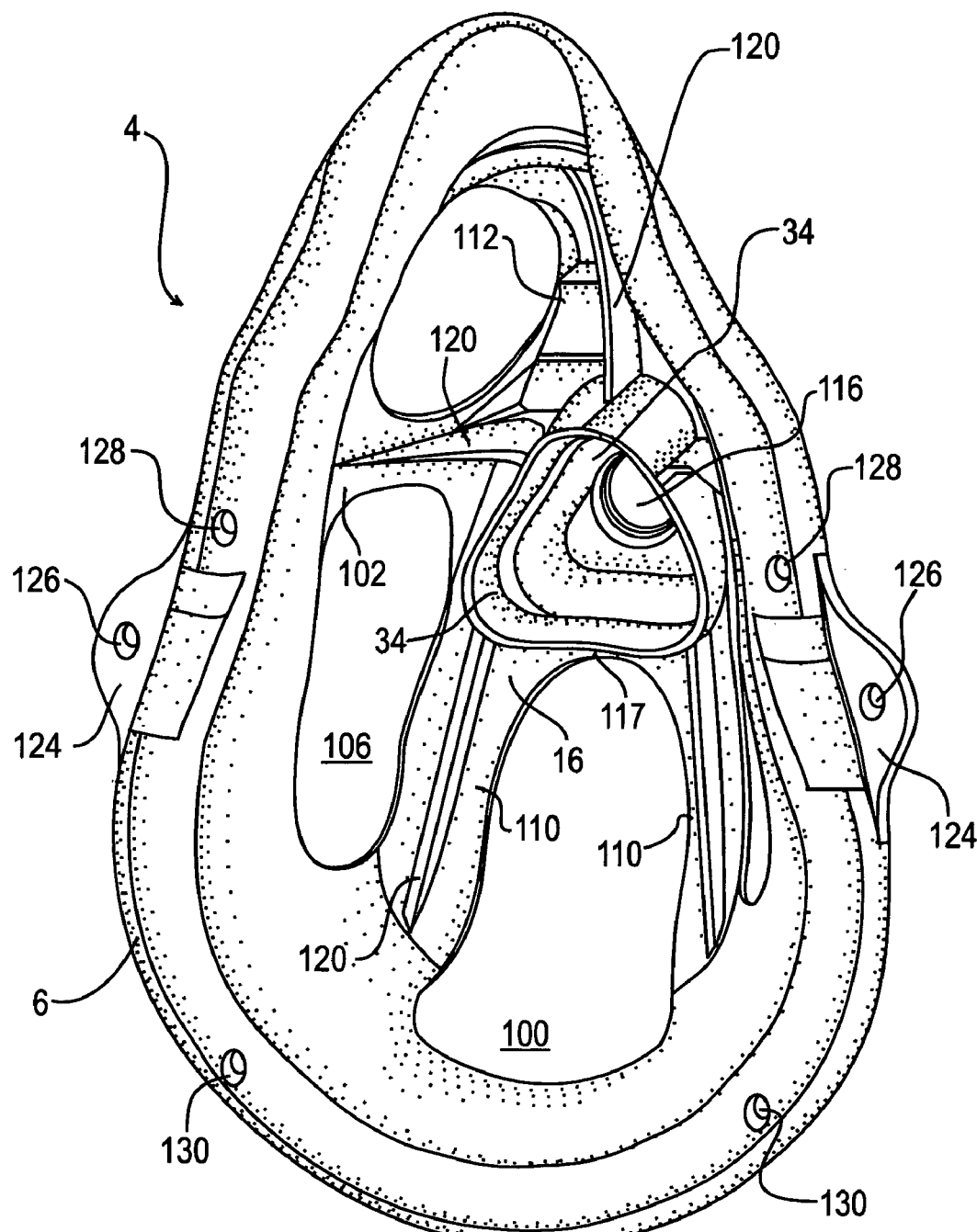
FIG. 7 is a perspective view of a still further embodiment of the mask.
Figure 8:
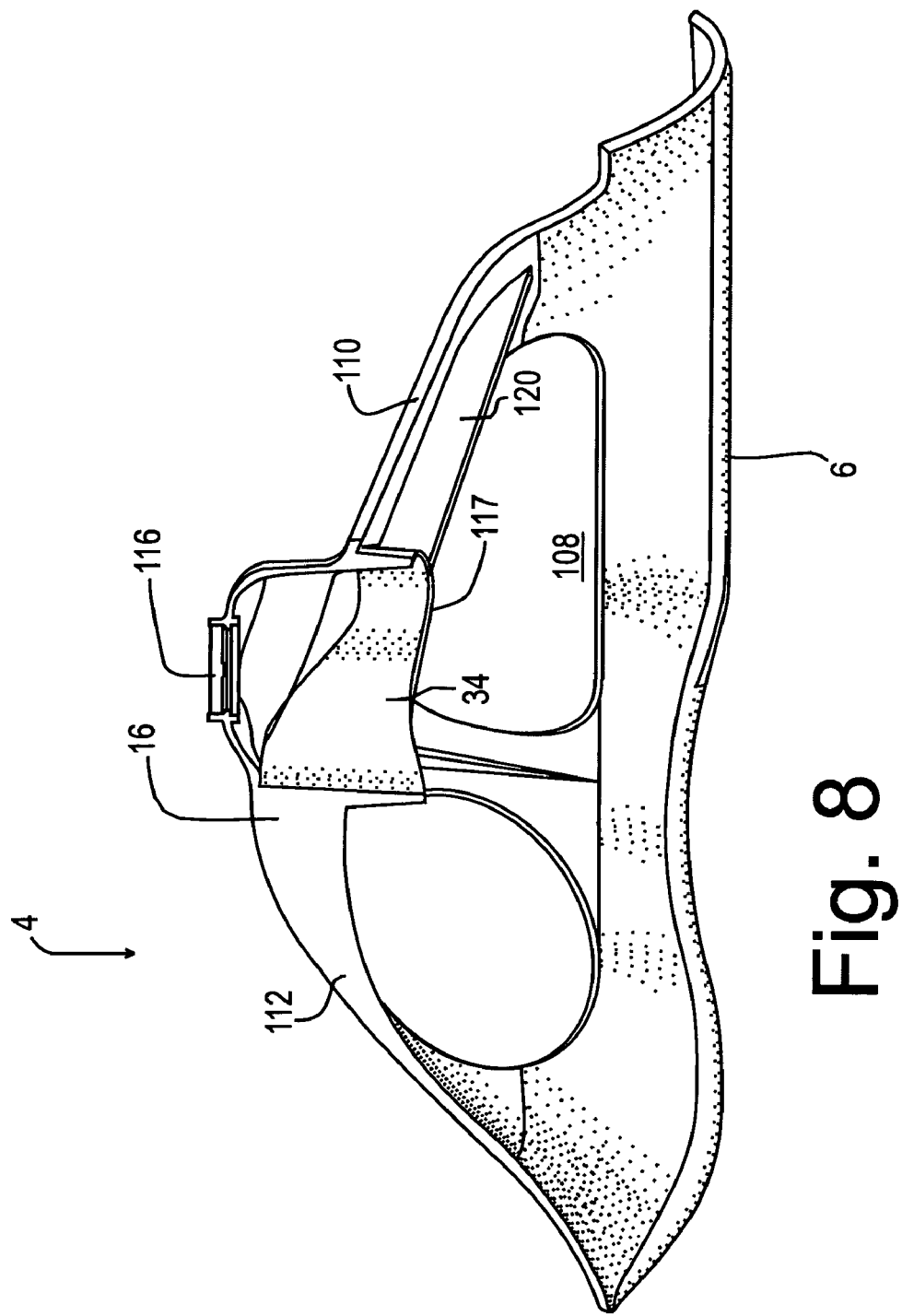
FIG. 8 is a side elevational view of the embodiment of FIG. 7.
Figure 9A:
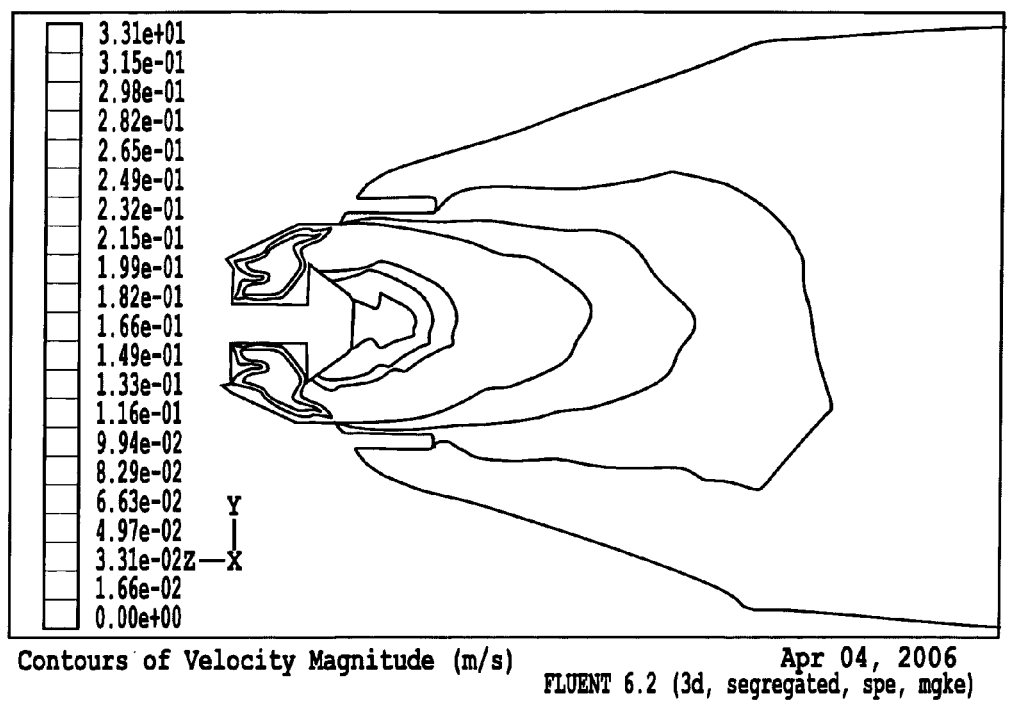
FIGS. 9 through 13 show simulations of gasses entering the mask of the embodiment of FIGS. 7 and 8, at varying flow rates.
Figure 9B:
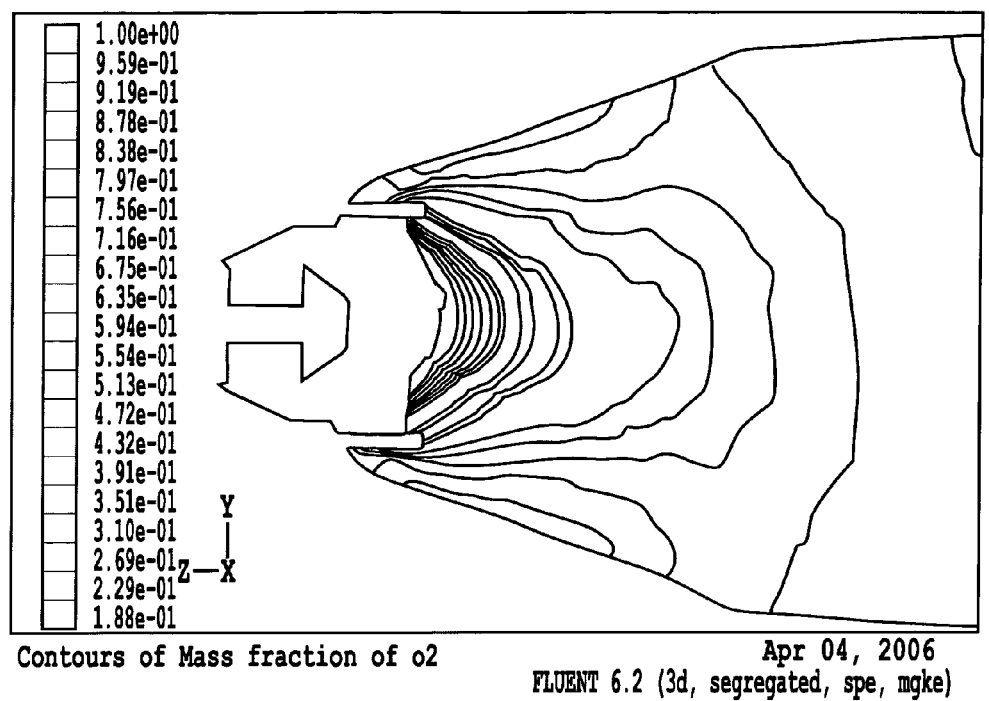
Figure 9C:
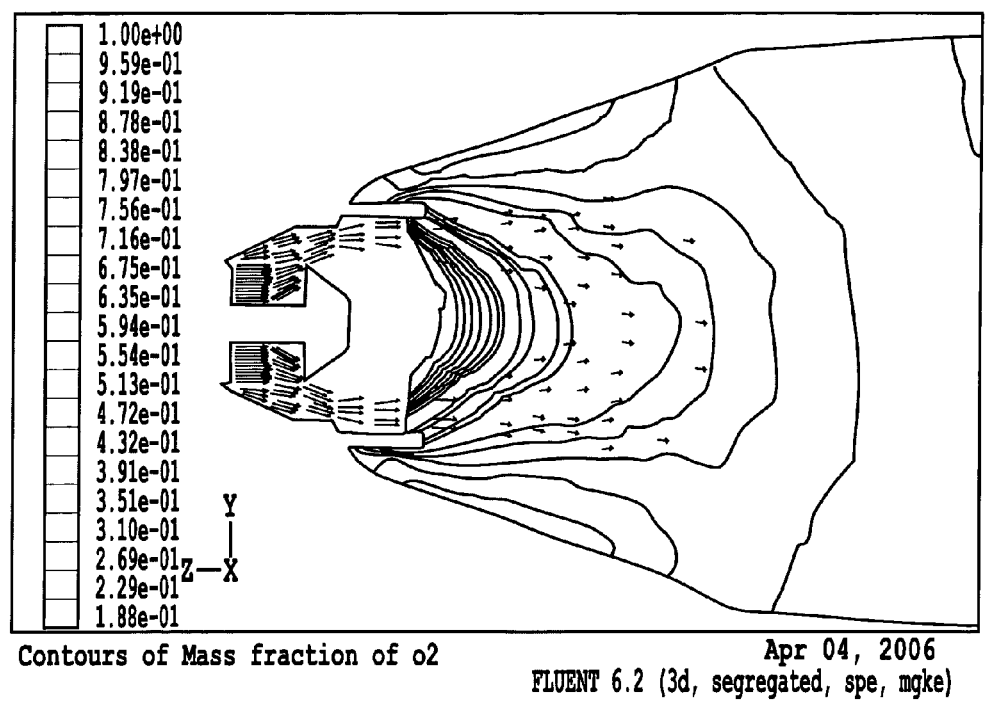
Figure 10A:
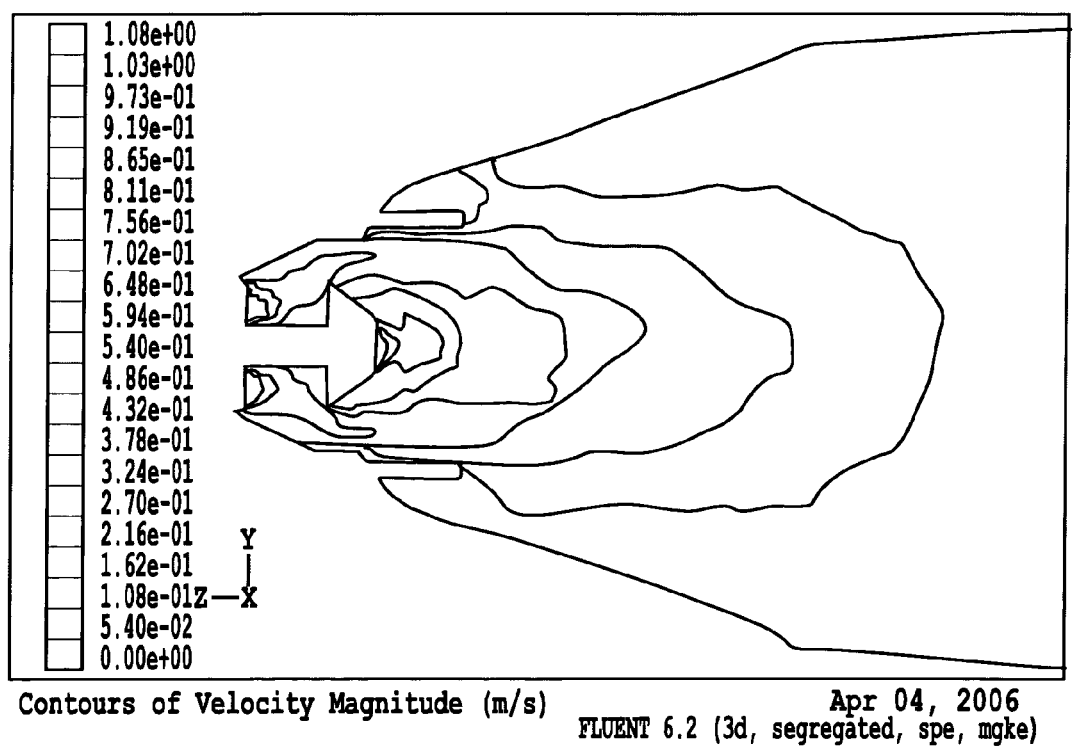
Figure 10B:
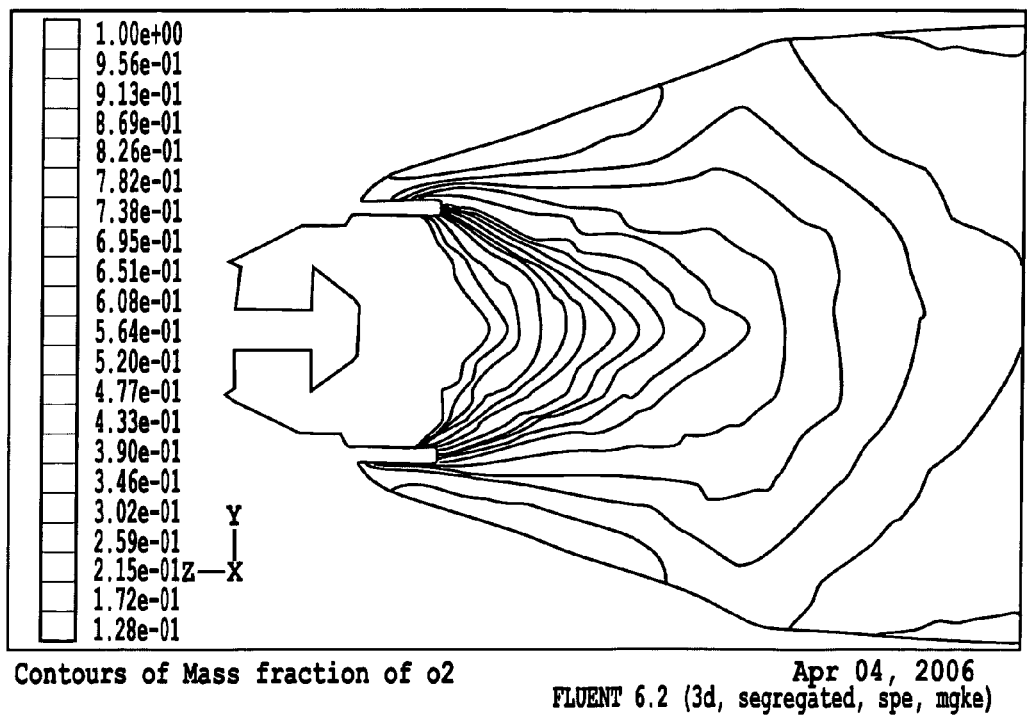
Figure 10C:
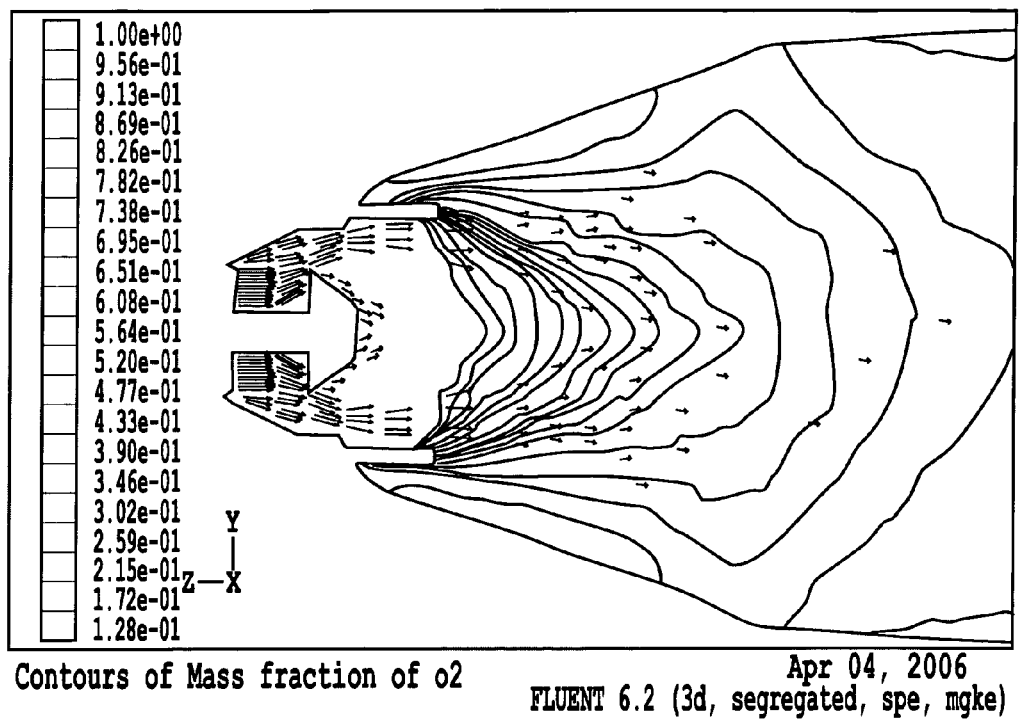
Figure 11A:
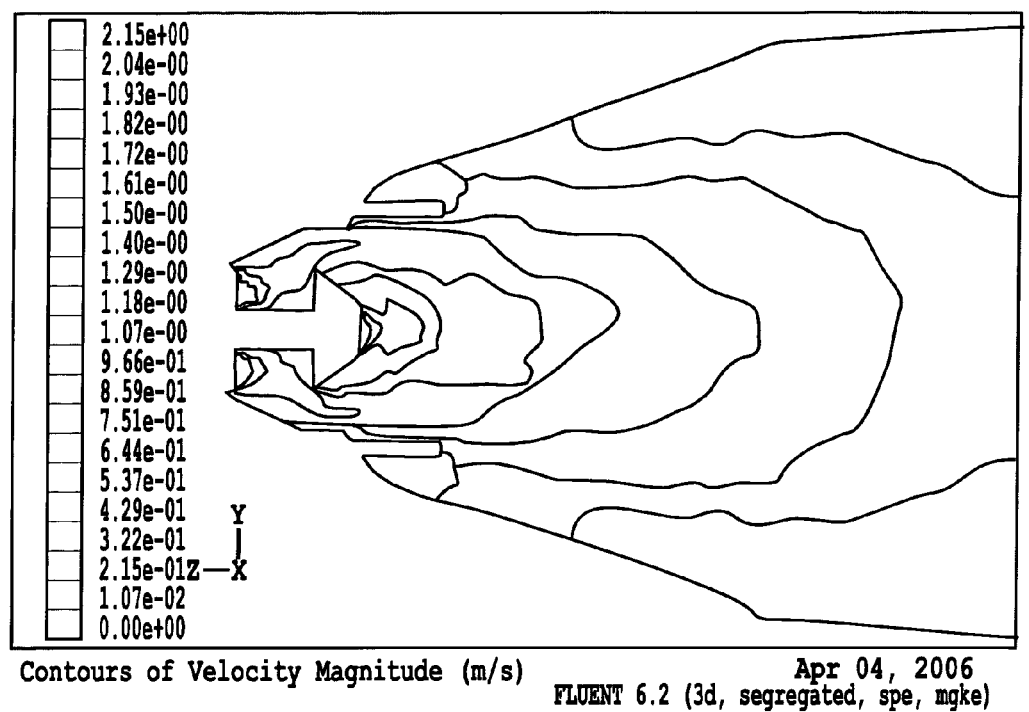
Figure 11B:
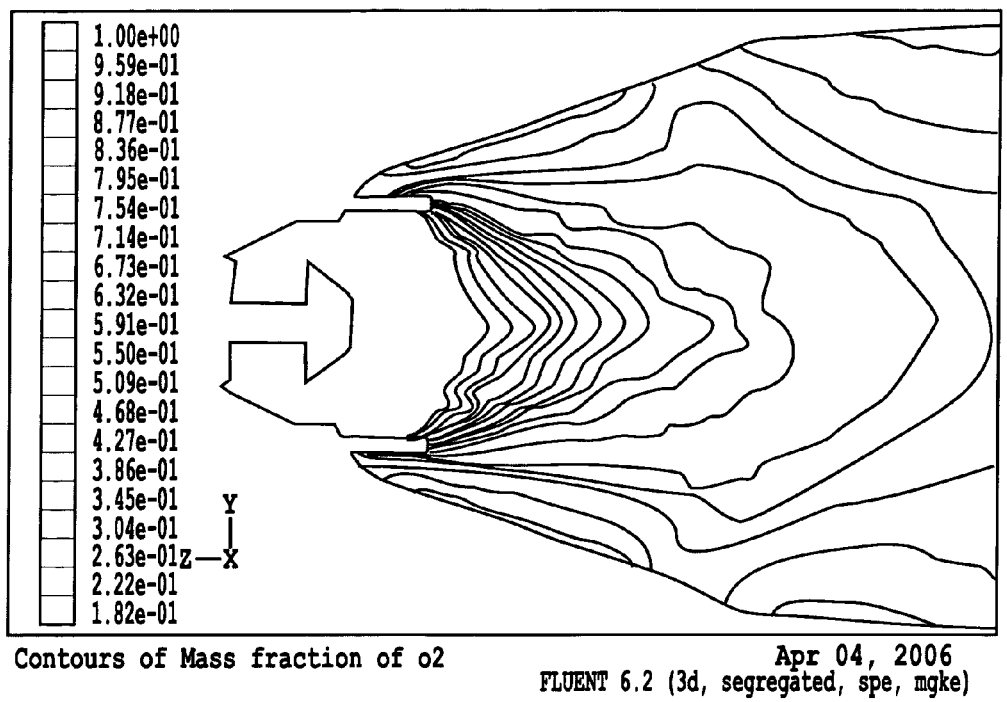
Figure 11C:
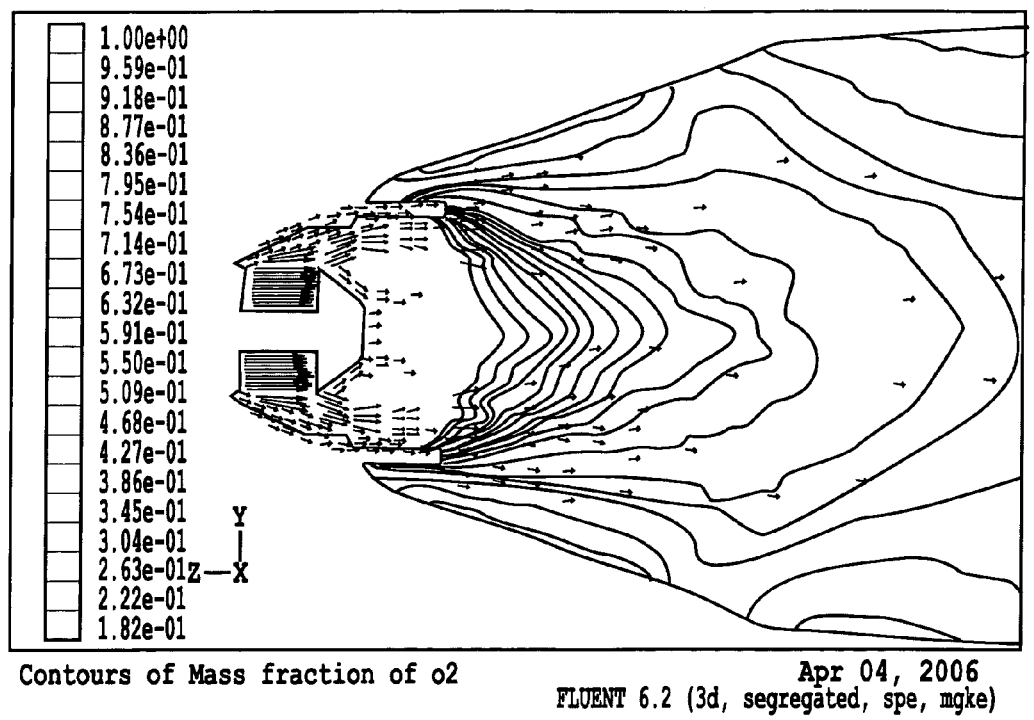
Figure 12A:
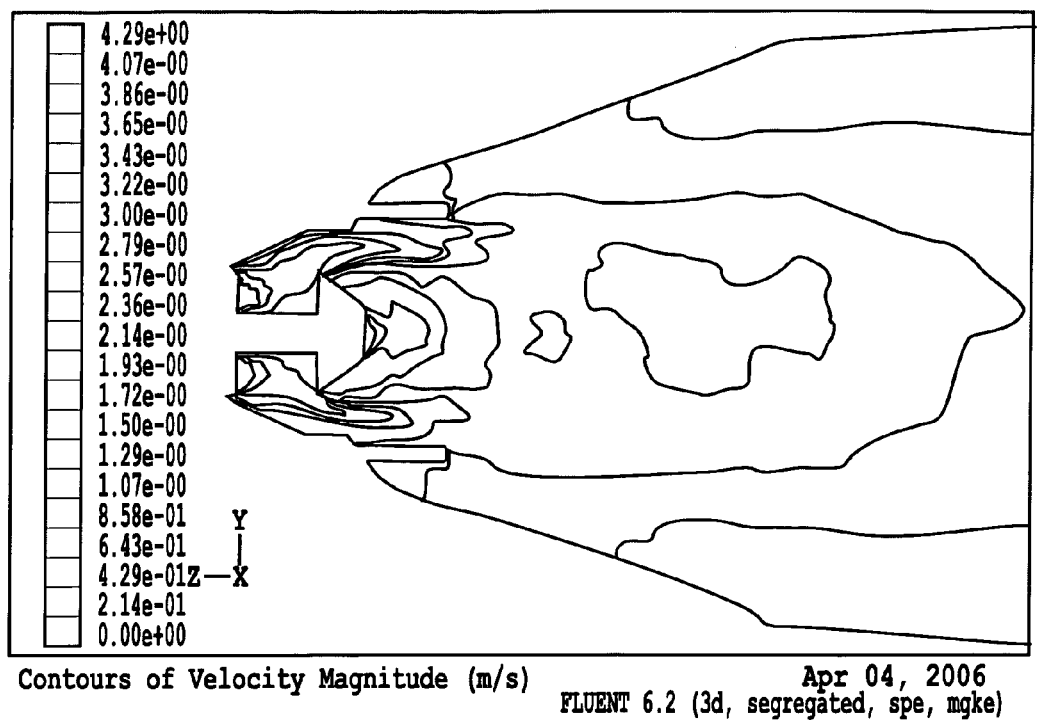
Figure 12B:
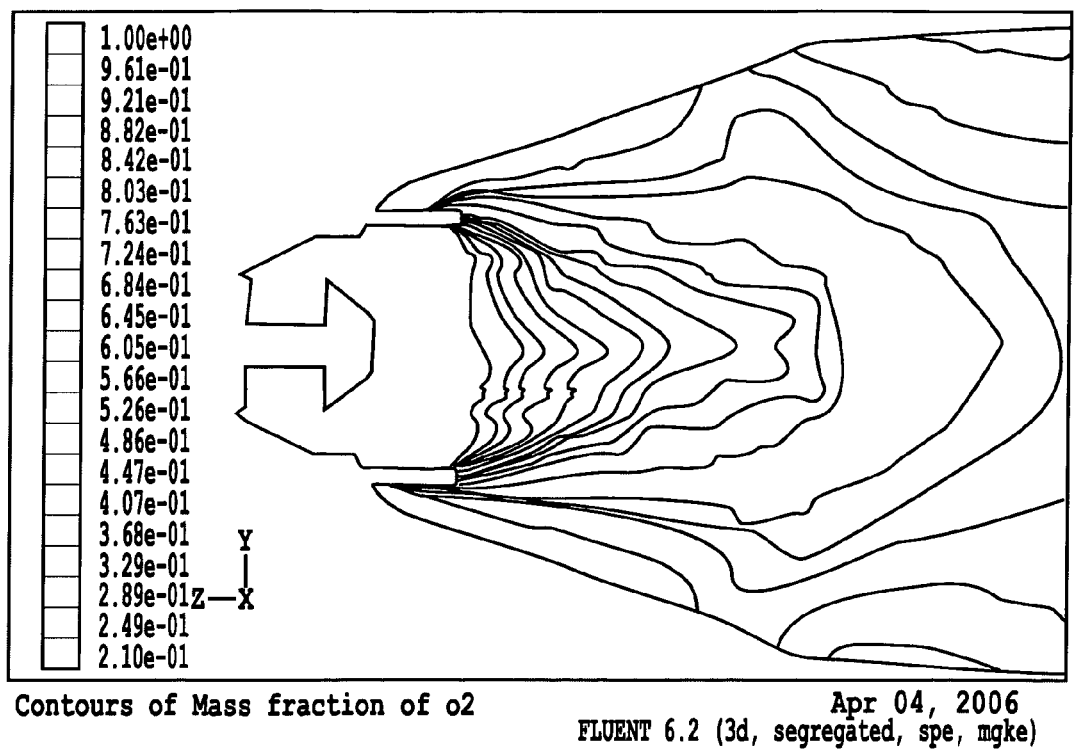
Figure 12C:
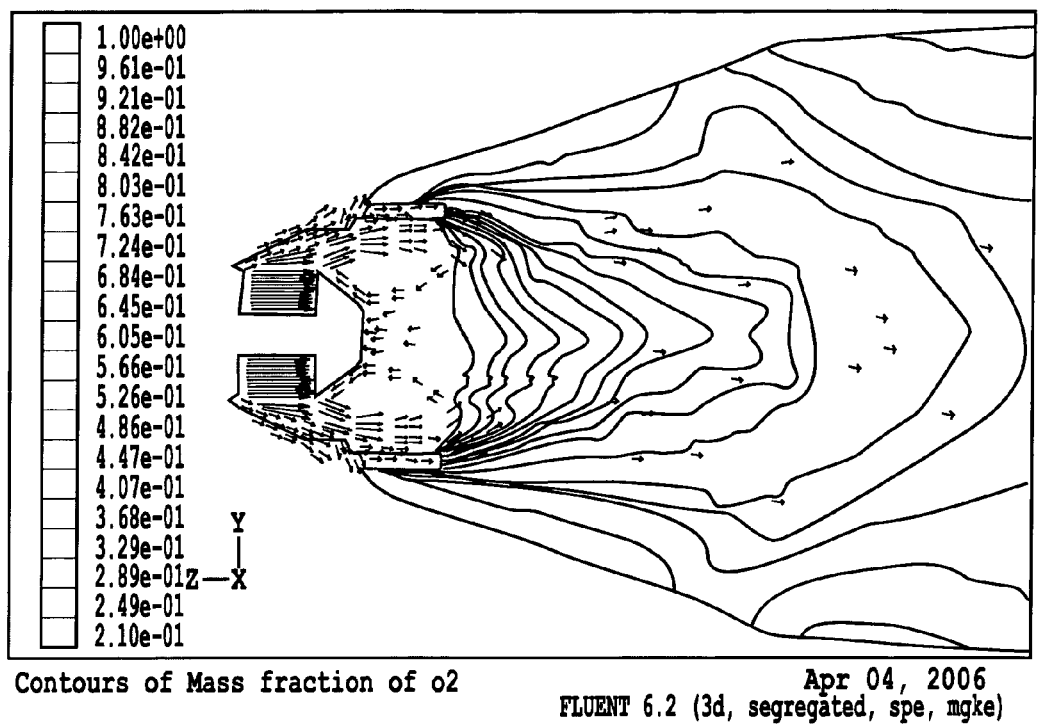
Figure 13A:
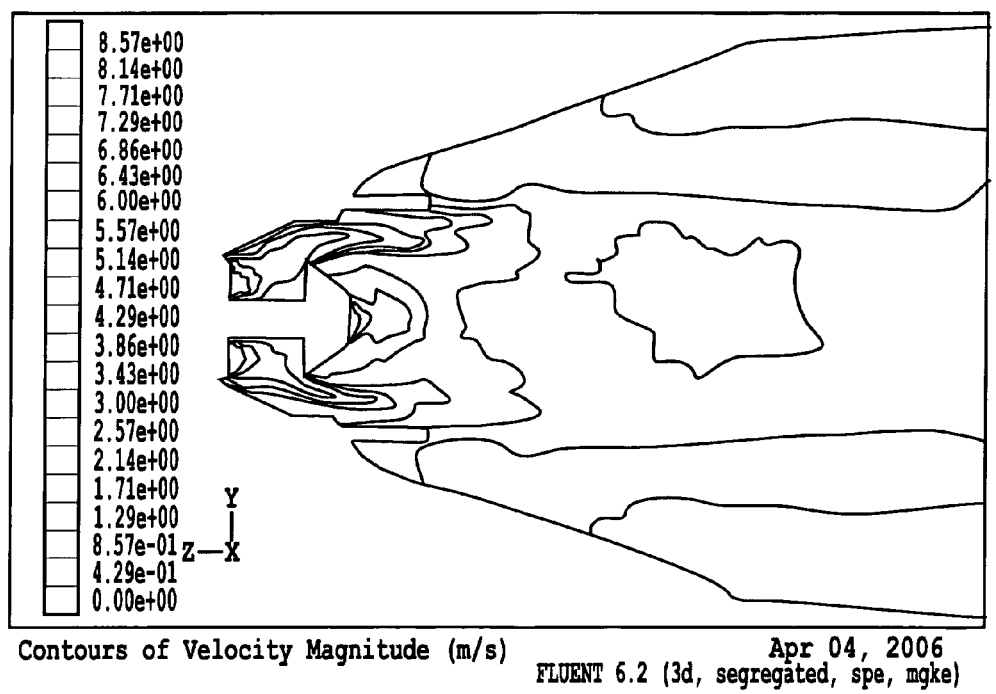
Figure 13B:
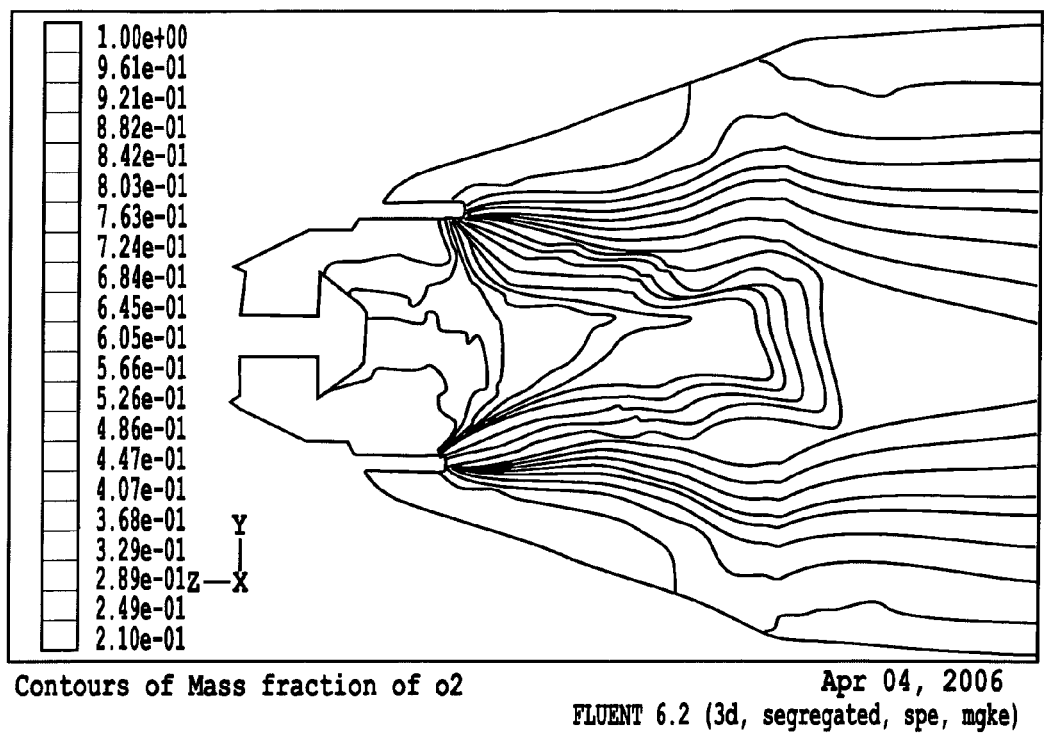
Figure 13C:
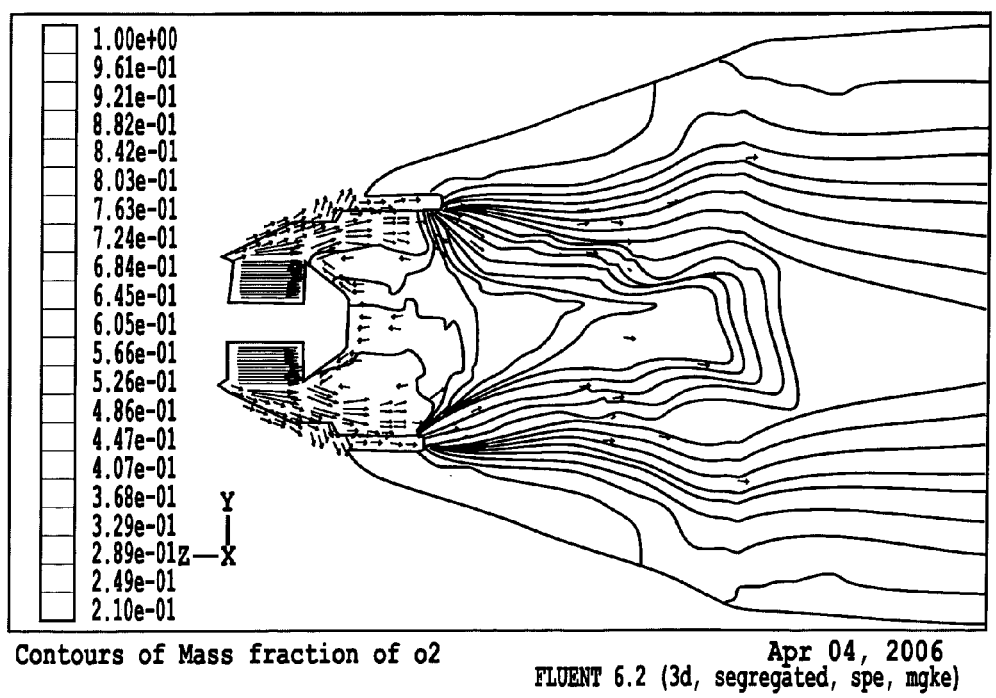

The data relating to the embodiments of FIGS. 7 and 8 thus shows that the parameters (good oxygen concentration and varied flow rates) can be achieved.

Low systems deliver 100% oxygen at flows that are less then the patient's inspiratory flow rate (i.e., the delivered oxygen is diluted with room air) and thus the oxygen concentration (FI02) may be high or low device and the patients rate.

In contrast, nasal cannula can provide 24-40% oxygen with flow rates up to 6 L/min but should be humidified at rates above 4 L/min.

At rates higher then 6 to 10 LPM and 40-70% oxygen require a partial re-breathing mask. This is considered a low flow system; a non re-breathing mask is similar to the partial re-breathing mask, except that it has a series of one-way valves. This requires a minimum flow of 10 L/min. The delivered FI02 of this system is 60-80%.

FIGS. 9 through 13 illustrate schematically the gas plume formed, at different flow rates, by the mask according to the final embodiment described herein. The simulations indicate how the shape of the oxygen enriched plume changes in concentration and distance from the diffuser at various flow rates, 1.5, 5.0 10.0 20.0 and 40 LPM (Liters/Minute).

Figure 14:
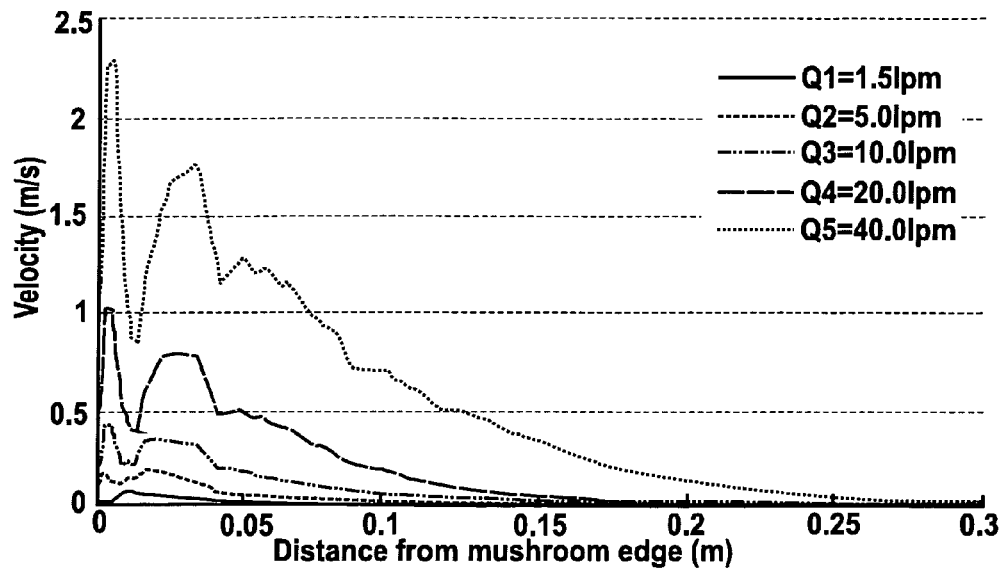
FIGS. 14 and 15 are graphs illustrating the behavior of gasses within the said embodiment of FIGS. 7 and 8.
Figure 15:
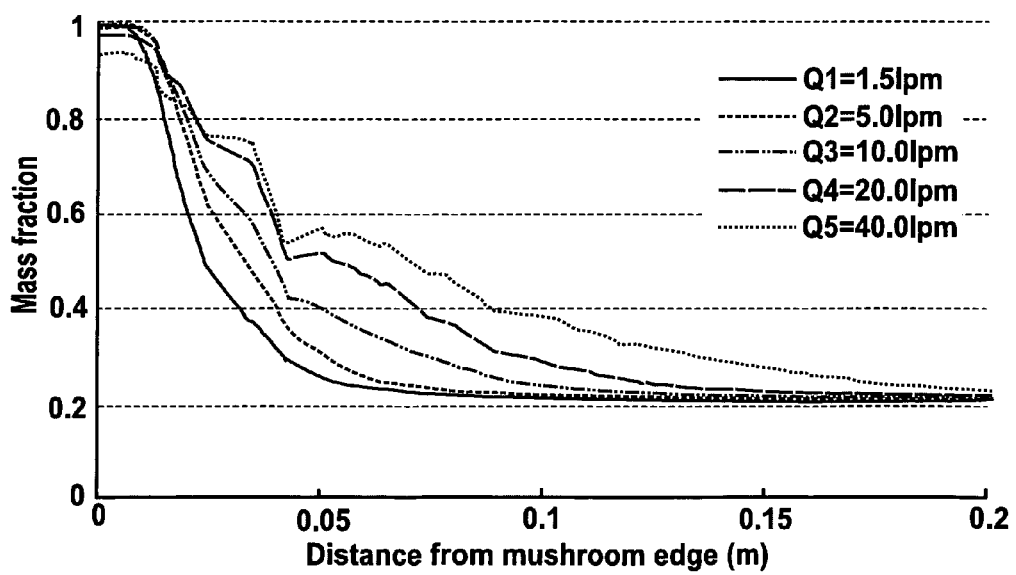
Figure 16:
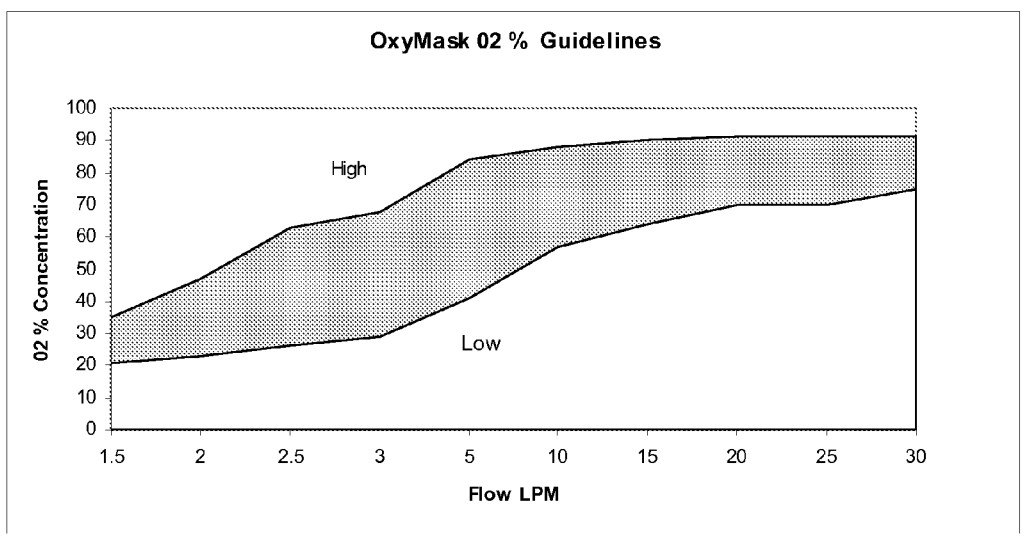
FIG. 16 is a graph showing the range of oxygen concentrations of the mask according to said embodiment plotted against flow rate.

FIG. 14 is a graph showing the gas velocity, at different flow rates, plotted against the distance from the end of the mushroom-shaped central baffle, in the embodiment described lastly herein. FIG. 15 is a graph showing the mass fraction, namely of the oxygen percentage which at ie 2.29 E-01 is 22.9%, plotted against the distance from the baffle towards the user's face, for different flow rates. In both cases, flow rates between 1.5 and 40 LPM were tested. FIG. 16 is a graph showing the range of oxygen concentration within the mask at flow rates between 1.5 LPM and 30 LPM.

As well, the mask design of the present invention allows a patient to drink, eat, be suctioned and speak, without removal of the mask. Also, exhaled air does not collect in the area in front of the patient's nose and mouth and interfere with the mask's operation, as in the case of conventional oxygen masks, since exhaled air easily passes to the surrounding environment through the spaces between the bridge portions and the peripheral portion of the mask.

In tests which have been done and proven the efficacy of the mask designs according to the present invention, it has been determined that patients find the mask according to the present invention to be far more comfortable than conventional oxygen masks. Unlike conventional masks, users cannot feel oxygen being delivered to their nose and mouth area, and enjoy the compactness of the mask. Technically, lower flow rates of oxygen to a patient through the mask of the present invention can be achieved, with as much or greater oxygen concentration in the air being delivered to the patient, as compared to conventional oxygen masks. In this manner, the mask according to the present invention provides both comfort and efficiency to patients which providing optimal blood oxygen saturation in a cost effective manner. Flow rates ranging from 0.5 Liters to 15 Liters per minute have proven suitable providing a far greater range of possible flow rates than available through conventional oxygen delivery devices. The following examples describe tests performed with the mask.

EXAMPLE 1

A study was conducted, comprising a randomized, crossover, single-blind study of patients having the following inclusion criteria:

chronic pulmonary disease requiring supplemental oxygen therapy;

stable oxygen requirement (unchanging over a three hour period);

18-80 years of age.

Excluded were patients whose oxygen requirement is unstable (i.e. changing hourly) or who could not tolerate being deprived of supplemental oxygen for five minutes or less.

Protocol

Continuous monitoring of minute ventilation (Respitrace), $SaO_2$, HR, nasal/oral flow, $PO_2$ and $PCO_2$ at the lip, $O_2$ flow and $TcPCO_2$:

5-10 min washout/5 min baseline (room air);

Mask #1 (supplemental oxygen; referred to herein as "OxyMask™ or "OM" and comprising an embodiment of the invention);

15-30 min at 4-5% above baseline $SaO_2$;

15-30 min at 8-9% above baseline $SaO_2$;

5-10 min washout/5 min baseline (room air);

Mask #2 (supplemental oxygen; referred to herein as "venturi" or "V", comprising a prior art mask);

15-50 min at 4-5% above baseline $SaO_2$;

15-30 min at 8-9% above baseline $SaO_2$.

Data analyzed using two-way analysis of variance (ANOVA) and paired t-test:

p values<0.05 were considered statistically significant.

Patient Demographics

N=13 patients with chronic pulmonary disease using supplemental oxygen via nasal cannula.

4 male, 9 female.

age: 56±16 (range: 28-79).

BMI: 35.0±12.3.

O2 requirement: 2.3±1.3 Lpm (rest), 3.4±1.6 Lpm (exercise).

Pulmonary Function Tests

| Spirometry | | |
|---|---|---|
| | Measured | % Predicted |
| FVC, L | 1.87 ± 0.66 | 57.38 ± 13.20 |
| FEV1, L | 1.22 ± 0.56 | 51.54 ± 21.50 |
| FEV1/FVC | 65.06 ± 19.29 | — |
| V50, L/sec | 1.38 ± 1.23 | 42.15 ± 34.71 |
| V25, L/sec | 0.40 ± 0.32 | 25.23 ± 18.66 |
| VC, L | 2.00 ± 0.80 | 60.20 ± 15.05 |

| Arterial Blood Gases | |
|---|---|
| pH | 7.38 ± 0.05 |
| H ion, nmol/L | 41.63 ± 5.01 |
| pCO2, mmHg | 47.50 ± 6.65 |
| pO2, mmHg | 50.88 ± 7.92 |
| Bicarbonate, mmol/L | 29.13 ± 4.70 |
| Measured O2 Saturation | 0.85 ± 0.06 |
| Base Excess, mmol/L | 2.26 ± 4.29 |

Results

| | Low Saturation | | High Saturation | | ANOVA | | |
|---|---|---|---|---|---|---|---|
| | OxyMask | Venturi | OxyMask | Venturi | Saturation Level | Mask | Interaction |
| $SaO_2$, % | 92.0 ± 3.6 | 91.7 ± 3.4 | 94.8 ± 3.2 | 94.9 ± 3.6 | — | NS | NS |
| Flow $O_2$, L/min | 0.9 ± 0.3 | 4.8 ± 1.5 | 2.1 ± 0.9 | 12.2 ± 3.9 | <0.01 | <0.01 | <0.01 |
| Ve, L/min | 9.1 ± 5.0 | 7.4 ± 4.2 | 10.6 ± 5.9 | 8.0 ± 4.4 | NS | <0.05 | NS |
| $T_cPCO_2$, mmHg | 51.9 ± 8.9 | 51.4 ± 7.6 | 51.3 ± 9.1 | 52.4 ± 8.0 | NS | NS | <0.05 |
| $P_IO_2$, mmHg | 229.7 ± 44.5 | 192.6 ± 11.9 | 459.5 ± 167.5 | 330.0 ± 126.6 | <0.01 | <0.01 | <0.05 |
| $P_EO_2$, mmHg | 164.4 ± 16.9 | 181.7 ± 12.2 | 209.2 ± 39.2 | 266.9 ± 52.4 | <0.05 | <0.01 | <0.05 |
| $P_ICO_2$, mmHg | 3.9 ± 1.5 | 1.6 ± 0.9 | 3.2 ± 0.6 | 1.4 ± 0.8 | <0.05 | <0.01 | NS |
| $P_ECO_2$, mmHg | 33.5 ± 8.9 | 11.3 ± 5.6 | 27.2 ± 8.9 | 11.6 ± 8.0 | <0.01 | <0.01 | <0.05 |
| HR, b/min | 77.9 ± 18.0 | 78.2 ± 17.9 | 78.9 ± 18.9 | 77.3 ± 17.7 | <0.05 | NS | NS |
| Nasal:Oral Flow | 1.20 ± 0.32 | 1.01 ± 0.26 | 1.11 ± 0.22 | 1.07 ± 0.26 | NS | NS | NS |

Summary $O_2$ flow rate significantly lower with OM vs. V.

$P_IO_2$ significantly higher and $P_EO_2$ significantly lower with OM. vs. V

Ve significantly higher with OM vs. V while $TcPCO_2$ similar between masks.

$P_ICO_2$ and $P_ECO_2$ significantly higher with OM vs. V.

Difference in $O_2$ flow remained significant when comparing patients whose Ve increased by >=10% with OM vs. V to those whose did not.

It is evident that many alternatives, modifications and variations will be apparent to those skilled in the art in light of the foregoing description. Accordingly, it is intended to embrace all such alternatives, modifications and variations as fall within the spirit and broad scope of the invention.

The invention claimed is:

1. A mask for delivery of gas to a patient from a source of pressurized gas, comprising: a mask body configured to enclose the patient's nose and mouth having a rim configured for contacting the patient's face; a gas inlet opening into said mask body to admit a gas stream from said source into the interior of said mask body; an L-shaped gas supply connector engaged to said gas inlet; a fastener adapted to maintain contact between the patient's face and the rim; and a diffuser within the interior of the mask body adapted to be located at a position opposed to and directed towards the user's nose and mouth, said diffuser comprising an upper wall portion and a lower wall portion, wherein the end of the lower wall portion is continuously formed with the mask body, said diffuser further surrounding said inlet defining a partially enclosed space, and said diffuser further comprising a baffle located at least partially within said space in the path of said gas stream, said baffle comprising a post and an enlarged head having a lip wherein the head fills a portion of the enclosed space of the diffuser and the lip is configured to generate a turbulent plume when contacted by the stream of gas, said diffuser adapted to be opposed to the patient's face and positioned within the mask such that the direction of gas flow exiting the diffuser is configured towards the patient's face in a non-oblique direction; and wherein said mask body comprises a substantially open structure having openings which altogether comprise between 30 and 80% of the mask body.

2. A mask as defined in claim 1 wherein said gas inlet comprises an annular opening surrounding the base of said post opening into said partially enclosed space.

3. A mask as defined in claim 1 wherein said baffle projects outwardly past the diffuser wall.

4. A mask as defined in claim 1 wherein said diffuser is configured to form a turbulent gas plume when said pressurized gas is delivered within a flow range of about 1.5 to about 30 liters per minute.

5. A mask as defined in claim 1 wherein said baffle is mushroom-shaped.

6. A mask as defined in claim 1 wherein said mask body further comprises an array of ribs projecting into the interior of said body and radiating outwardly from said diffuser wall.

7. A mask as defined in claim 1 wherein said diffuser wall and baffle form a nesting cup configuration wherein said diffuser wall comprises an outer cup and said baffle comprises an inner cup.

8. The mask of claim 1 wherein said diffuser is configured and located within the mask to fit entirely within a space defined in relation to a point on the patient's face about halfway between the base of the patient's nose and the patient's upper lip when the mask is worn in the upright position, said space defined vertically as 40 mm above and below said point to direct gas directly towards the patient's nose and mouth.

9. A mask for delivery of gas to a patient from a source of pressurized gas, comprising: a mask body configured to enclose the patient's nose and mouth and a rim configured for contacting the patient's face; a fastener adapted to maintain contact between the patient's face and the rim, said mask body comprising a substantially open structure having openings which altogether comprise between 30 and 80% of the mask body; a gas inlet opening into said mask body to admit a gas stream from said source into the interior of said mask body; an L-shaped gas supply connector engaged to said gas inlet; a connector attached to said mask body for connection to a $CO_2$ sampling tube; and a diffuser comprising an upper wall portion and a lower wall portion, wherein the end of the lower wall portion is continuously formed with the mask body, said diffuser further surrounding said gas inlet defining a partially enclosed space and a baffle located in the path of said gas stream and having a passageway therein, said baffle comprising a post and an enlarged head having a lip wherein the head fills a portion of the enclosed space of the diffuser wherein the lip generates a turbulent plume from the stream of gas, said diffuser adapted to be opposed the patient's face and positioned within the mask such that the direction of gas flow exiting the diffuser is configured towards the patient's face in a non-oblique direction; said passageway communicating with said $CO_2$ sampling connector and having an open end configured to admit exhaled breath from the patient; wherein said baffle and diffuser are configured to generate a turbulent plume of directed towards the patient when said gas enters said inlet, while permitting breath discharge by said patient to be received within the open end of said passageway.

10. A mask as defined in claim 9 wherein said gas inlet comprises an annular opening around said $CO_2$ connector configured to deliver said gas stream from said pressurized source into said partially enclosed space.

11. A mask as defined in claim 9 wherein said baffle projects outwardly past the diffuser wall.

12. A mask as defined in claim 9 wherein said baffle fills a substantial portion of the interior of said diffuser wall and said gap comprises an annular space.

13. A mask as defined in claim 9 wherein said diffuser wall and baffle form a nesting cup configuration wherein said diffuser wall comprises an outer cup and the baffle comprises an inner cup.

14. A mask as defined in claim 9 wherein said diffuser is configured to form said turbulent gas plume when said pressurized gas is delivered within a flow range of about 1.5 to about 30 liters per minute.

15. A mask as defined in claim 9 wherein said baffle is mushroom-shaped.

16. A mask as defined in claim 9 wherein said mask body further comprises an array of ribs projecting into the interior of said body and radiating outwardly from said diffuser wall.

17. A mask as defined in claim 9 further comprising a $CO_2$ sampling tube engaged to said $CO_2$ connector.

* * * * *